(12) United States Patent
Kamal et al.

(10) Patent No.: US 9,029,553 B2
(45) Date of Patent: May 12, 2015

(54) 2-ANILINO NICOTINYL LINKED 2-AMINO BENZOTHIAZOLE CONJUGATES AND PROCESS FOR THE PREPARATION THEREOF

(75) Inventors: Ahmed Kamal, Hyderabad (IN); Yellamelli Valli Venkata Srikanth, Hyderabad (IN); Mohammed Naseer Ahmed Khan, Hyderabad (IN); Mohammed Ashraf, Hyderabad (IN); Irum Sehar, Jammu (IN); Gousia Chashoo, Jammu (IN); Parduman Raj Sharma, Jammu (IN); Abid Hamid Dar, Jammu (IN); Bhushan Shashi, Jammu (IN); Shashank Kumar Singh, Jammu (IN); Dilip Manikrao Mondhe, Jammu (IN); Ajit Kumar Saxena, Jammu (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/985,417

(22) PCT Filed: Mar. 30, 2011

(86) PCT No.: PCT/IN2011/000217
§ 371 (c)(1),
(2), (4) Date: Aug. 14, 2013

(87) PCT Pub. No.: WO2012/111016
PCT Pub. Date: Aug. 23, 2012

(65) Prior Publication Data
US 2013/0324734 A1 Dec. 5, 2013

(30) Foreign Application Priority Data
Feb. 14, 2011 (IN) .............................. 373/DEL/2011

(51) Int. Cl.
C07D 417/12 (2006.01)
A61K 31/4439 (2006.01)
A61P 35/00 (2006.01)

(52) U.S. Cl.
CPC .................................. C07D 417/12 (2013.01)

(58) Field of Classification Search
CPC ... C07D 213/74; C07D 277/83; A61K 31/381
USPC .......................................... 514/338; 546/270.1
See application file for complete search history.

(56) References Cited

U.S. PATENT DOCUMENTS 7,105,682 B2 * 9/2006 Chen et al. .................. 546/277.1
7,507,748 B2 * 3/2009 Yuan ............................. 514/310

FOREIGN PATENT DOCUMENTS

WO 2007123939 A2 11/2007

OTHER PUBLICATIONS

Patel; Oriental J. Chem., 2006, 22, 333-338.*
(Continued)

*Primary Examiner* — John Mabry
*Assistant Examiner* — Daniel Carcanague
(74) *Attorney, Agent, or Firm* — St. Onge Steward Johnston & Reens LLC

(57) ABSTRACT

The present invention provides compounds of general formula A useful as potential anticancer agents against human cancer cell lines and apoptosis inducers. The present invention further provides a process for the preparation of 2-anilino nicotinyl linked 2-amino benzothiazole conjugates of general formula (A), wherein $R^1$=H or Cl; $R^2$=H, $OCH_3$ or F; $R^3$=H, $OCH_3$, F or Cl; $R^4$=H, $OCH_3$ or F and X=$OCH_3$, F or $NO_2$.

6 Claims, 14 Drawing Sheets

(56) References Cited

OTHER PUBLICATIONS

Kamal; Bioorg. Med. Chem., 2007, 15, 1004-1013.*
Wermuth; Practice of Medicinal Chemistry 3rd ed 2008 chapter 20 pp. 429-463.*

International Search Report and Written Opinion of the International Searching Authority Application No. PCT/IN2011/000217 Completed: Jul. 15, 2011; Mailing Date: Jul. 21, 2011 12 pages.

* cited by examiner

2-ANILINO NICOTINYL LINKED 2-AMINO BENZOTHIAZOLE CONJUGATES AND PROCESS FOR THE PREPARATION THEREOF

FIELD OF THE INVENTION

The present invention relates to 2-anilino nicotinyl linked 2-amino benzothiazole of general formula A as potential anticancer agents and apoptosis inducers.

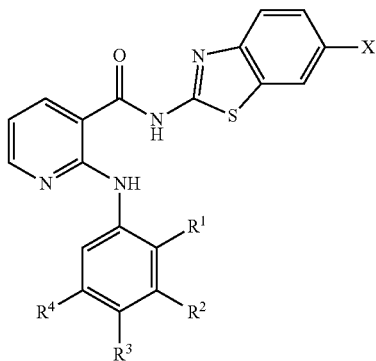

General formula A wherein $R^1$=H or Cl; $R^2$=H, $OCH_3$ or F; $R^3$=H, $OCH_3$, F or Cl; $R^4$=H, $OCH_3$ or F and X=$OCH_3$, F or $NO_2$ Present invention further relates to process for the preparation of 2-anilino nicotinyl linked 2-amino benzothiazole of general formula A.

BACKGROUND OF THE INVENTION

Cancer has become one of the major global health concerns and remains as the second cause of mortality after cardiovascular diseases. Cancer is a group of malignancies and characterized by uncontrolled cell growth in which cells lose their communication with surroundings and ignore the cell signaling. Chemoresistance is an important phenomenon associated with the cell division. In addition, safety profile and side effects are the major concerns with anticancer drugs. Therefore, the development of novel agents with increased efficacy while reducing the side effects will encourage the researchers towards the drug design and development.

Nuclear condensation and DNA fragmentation with various biological and cytological processes are involved in apoptosis. The extrinsic pathway of apoptosis involves binding of death activators to receptors such as tumor necrosis factor TNF-Rα and an intrinsic or mitochondrial pathway involves the initiation of apoptosis by chemotherapeutic agents as well as genotoxic stress and other death stimuli. (How cells die: apoptosis pathways. Zimmermann, K. C.; Green, D. R. J. Allergy. Clin. Immunol. 2001, 108, S99-S103). Caspases are a family of cysteine protease and are known to play a critical role for the initiation and execution of apoptosis (Caspase function in programmed cell death. Kumar, S. Cell Death Differ. 2007, 14, 32-43). Amongst the caspases, caspase-3, -6, and -7 are key effector caspases that cleave multiple protein substrates in cells ° leading to irreversible cell death (Caspases: Key mediators of apoptosis. Thornberry, N. A. Chem. Biol. 1998, 5, R97-R103).

E7010 (1, N-[2-[(4-hydroxyphenyl)amino]-3-pyridinyl]-4-methoxybenzene sulfonamide, FIG. 1B), an orally active sulfonamide antitumor agent that is currently in a Phase I clinical trial, showed rather consistent growth-inhibitory activities against a panel of 26 human tumor cell lines. This compound causes cell cycle arrest and apoptosis in M phase and is shown to exhibit microtubule assembly owing to its reversible binding to the colchicines binding site on tubulin. E7010 also exhibited good in vivo antitumor activity against various rodent tumor and human tumor xenografts and reached the clinical studies phase II it caused a dose-dependent increase in the percentage of mitotic cells in parallel with a decrease in cell proliferation (Mechanism of action of E7010, an orally active sulfonamide antitumor agent: inhibition of mitosis by binding to the colchicine site of tubulin. Yoshimatsu, K.; Yamaguchi, A.; Yoshino, H.; Koyanagi, N.; Kitoh, K. Cancer Res. 1997, 57, 3208-3213 and Mauer, A. M.; Cohen, E. E.; Ma, P. C.; Kozloff, M. F.; Schwartzberg, L.; Coates, A. I.; Qian, J.; Hagey, A. E.; Gordon, G. B. J. Thorac. Oncol., 2008, 3, 631-636). N-(2-Anilino-pyridyl) moiety, which exhibited interesting antitumor activity and some of these analogues are undergoing clinical trials (Novel sulfonamides as potential, systemically active antitumor agents. Yoshino, H.; Ueda, N.; Niijima, J.; Sugumi, H.; Kotake, Y.; Koyanagi, N.; Yoshimatsu, K.; Asada, M.; Watanabe, T.; Nagasu, T. J. Med. Chem. 1992, 35, 2496-2497); (In vivo tumor growth inhibition produced by a novel sulfonamide, E7010, against rodent and human tumors. Koyanagi, N.; Nagasu, T.; Fujita, F.; Watanabe, T.; Tsukahara, K.; Funahashi, Y.; Fujita, M.; Taguchi, T.; Yoshino, H.; Kitoh, K. Cancer Research. 1994, 54, 1702-1706); (Synthesis and structure-activity relationships of novel 7-substituted 1,4-dihydro-4-oxo-1-(2-thiazolyl)-1,8-naphthyridine-3-carboxylic acids as antitumor agents. Part 2. Tsuzuki, Y.; Tomita, K.; Shibamori, K.; Sato, Y.; Kashimoto, S.; Chiba, K. J. Med. Chem. 2004, 47, 2097-2109).

Carbonic anhydrase (CA) plays an essential role in facilitating the transport of carbon dioxide and protons in the intracellular space, across biological membranes and in the layers of the extracellular space. Ethoxazolamide (2 shown in FIG. 1B) a benzothiazole sulfonamide inhibits CA activity in proximal renal tubules to decrease reabsorption of water, sodium, potassium, bicarbonate. Ethoxazolamide and its structurally similar related analoges have shown to exhibit excellent anticancer activity by inhibiting CA and some of them are in clinical trials (The compound 6-ethoxy-1,3-benzothiazole-2-sulfonamide (ethoxazolamide) showed good antitumor profile. Vullo, D.; Franchi, M.; Gallori, E.; Antel, J.; Scozzafava, A.; Supuran, C. T. J. Med. Chem. 2004, 47, 1272-1279). Benzothiazoles are known to possess interesting anticancer activity (Antitumor benzothiazoles. 7. Synthesis of 2-(4-acylaminophenyl) benzothiazoles and investigations into the role of acetylation in the antitumor activities of the parent amines. Chua, M. S.; Shi, D. F.; Wrigley, S.; Bradshaw, T. D.; Hutchinson, I.; Shaw, P. N.; Barrett, D. A.; Stanley, L. A.; Stevens, M. F. J. Med. Chem. 1999, 42, 381-392); (Antitumor benzothiazoles. 8. Synthesis, metabolic formation, and biological properties of the C- and N-oxidation products of antitumor 2-(4-aminophenyl) benzothiazoles. Kashiyama, E.; Hutchinson, I.; Chua, M. S.; Stinson, S. F.; Phillips, L R.; Kaur, G.; Sausville, E. A.; Bradshaw, T. D.; Westwell, A. D.; Stevens, M. F. *J. Med. Chem.* 1999, 42, 4172-4184); (Antitumor benzothiazoles. 26. 2-(3,4-dimethoxyphenyl)-5-fluorobenzothiazole (GW 610, NSC 721648), a simple fluorinated 2-arylbenzothiazole, shows potent and selective inhibitory activity against lung, colon, and breast cancer cell lines. Mortimer, C. G.; Wells, G.; Crochard, J. P.; Stone, E. L.; Bradshaw, T. D.; Stevens, M. F.; Westwell, A. D. *J. Med. Chem.* 2006, 49, 179-185. (N-(cycloalkylamino) acyl-2-aminothiazole inhibitors of cyclin-dependent kinase 2. N-[5-[[[5-(1,1-dimethylethyl)-2-oxazolyl]methyl]thio]-2-thiazolyl]-4-piperidine carboxamide (BMS-387032), a highly efficacious and selective antitumor agent. Misra, R. N.; Xiao, H. Y.; Kim, K. S; Lu, S.; Han, W. C.; Barbosa, S. A.; Hunt, J. T.; Rawlins, D. B.; Shan, W.; Ahmed, S. Z.; Qian, L.; Chen, B. C.; Zhao, R.; Bednarz, M. S.; Kellar, K. A.; Mulheron, J. G.; Batorsky, R.; Roongta, U.; Kamath, A.; Marathe, P.; Ranadive, S. A.; Sack, J. S.; Tokarski, J. S.; Pavletich, N. P.; Lee, F. Y.; Webster, K. R.; Kimball, S. D. *J. Med. Chem.* 2004, 47, 1719-1728); (Novel benzothiazolyl urea and thiourea derivatives with potential cytotoxic and antimicrobial activities. Abdel-Rahman, H. M.; Morsy, M. A. *J. Enzyme Inhib. Med. Chem.* 2007, 22, 57-64). 2-(4-Aminophenyl) benzothiazoles and 2-(4-hydroxyphenyl) benzothiazoles are novel class of potent and selective antitumour agents and found to exhibit antitumor activity particularly against certain breast carcinoma cell lines in vitro (e.g., MCF-7, MDA 468, $IC_{50}$<1 nM) to be promising anticancer activity (Antitumor Benzothiazoles. 3. Synthesis of 2-(4-Aminophenyl) benzothiazoles and evaluation of their activities against Breast Cancer Cell Lines in vitro and in vivo. Shi, D. F.; Bradshaw, T. D.; Wrigley, S.; McCall, C. J.; Lelieveld, P.; Fichtner, I.; Stevens, M. F. J. Med. Chem. 1996, 39, 3375-3384); (Antitumor Benzothiazoles. 14. Synthesis and in vitro biological properties of fluorinated 2-(4-Aminophenyl)benzothiazoles. Hutchinson, A.; Chua, M.; Browne, H. L.; Trapani, V.; Bradshaw, T. D; Westwell, A. D; Stevens, M. F. J. Med. Chem. 2001, 44, 1446-1455).

Many synthetic analogs containing sulfonamides with incorporated hydrazine moieties (3 shown in FIG. 1B) have shown promising anticancer activity (Synthesis of a new class of 2-anilino substituted nicotinyl arylsulfonylhydrazides as potential anticancer and antibacterial agents. Kamal, A.; Khan, M. N. A.; Reddy, K. S.; Rohini, K. *Bioorg. Med. Chem.* 2007, 15, 1004-1013) Keeping this aspect in mind, 2-amino benzothiazole rings system has been linked to N-(2-anilinopyridyl) scaffold, therefore, the newly designed and synthesized molecules comprising of benzothiazoles and 2-anilinopyridyl moiety could possess promising anticancer activity: Additionally, these are structurally simple small molecules.

OBJECTIVE OF THE INVENTION

The main objective of the present invention is to provide 2-anilino nicotinyl linked 2-amino benzothiazole conjugates of general formula A useful as potential anticancer agents and apoptosis inducers.

Yet another objective of the present invention is to provide process for the preparation of 2-anilino nicotinyl linked amino benzothiazole conjugates of general formula A.

SUMMARY OF THE INVENTION

Accordingly, the present invention provides 2-anilino nicotinyl linked 2-amino benzothiazole conjugates of general formula A

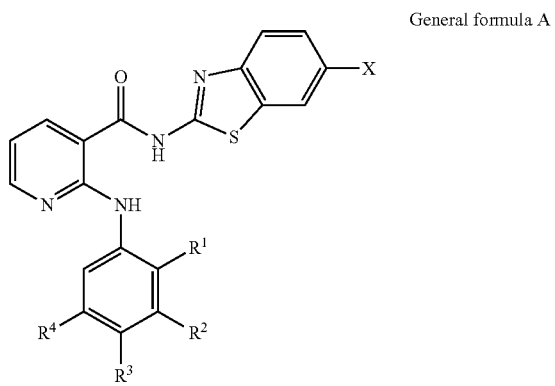

General formula A wherein $R^1$=H or Cl; $R^2$=H, $OCH_3$ or F; $R^3$=H, $OCH_3$, F or Cl; $R^4$=H, $OCH_3$ or F and X=$OCH_3$, F or $NO_2$.

In an embodiment of the present invention, representative compounds comprising:
N3-(6-nitro-1,3-benzothiazol-2-yl)-2-(phenylamino)-3-pyridinecarboxamide (4);
N3-(6-nitro-1,3-benzothiazol-2-yl)-2-(4-methoxyanilino) nicotinamide (5);
N3-(6-nitro-1,3-benzothiazol-2-yl)-2-(4-fluoroanilino)nicotinamide (6);
N3-[6-(nitro-1,3-benzothiazol-2-yl]-2-[(2,4-dichlorophenyl)amino]-3-pyridinecarboxamide (7);
N3-(6-nitro-1,3-benzothiazol-2-yl)-2-[(3,4,5-trifluorophenyl)amino]-3-pyridine carboxamide (8);
N3-(6-fluoro-1,3-benzothiazol-2-yl)-2-(4-fluoroanilino) nicotinamide (9);
N3-(6-fluoro-1,3-benzothiazol-2-yl)-2-(2,4-dichloroanilino) nicotinamide (10);
N3-(6-fluoro-1,3-benzothiazol-2-yl)-2-(3,4,5-trimethoxyanilino)nicotinamide (11);
N3-(6-methoxy-1,3-benzothiazol-2-yl)-2-(3,4,5-trimethoxyanilino)nicotinamide (12).

In another embodiment of the present invention, structural formula of the representative compounds are:

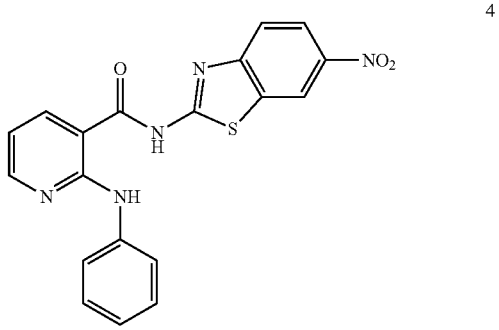

4

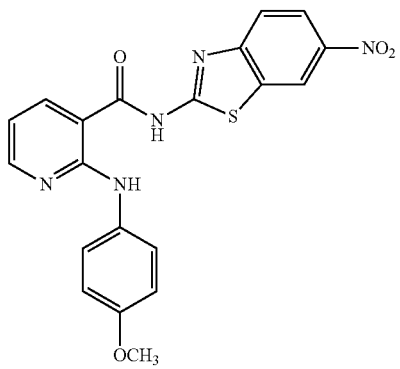
5
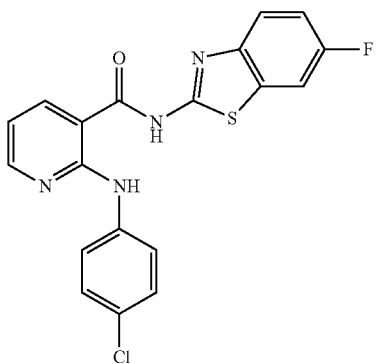
9
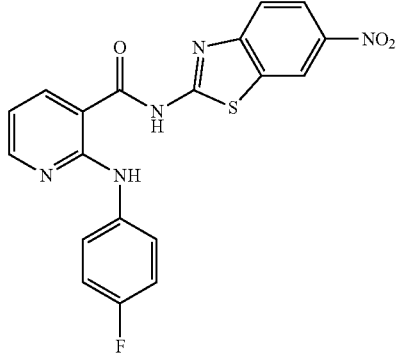
6
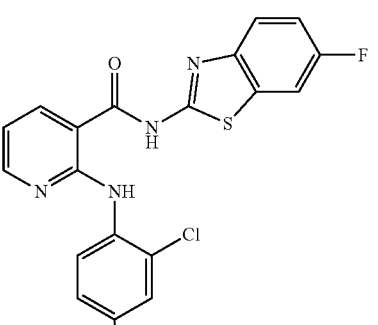
10
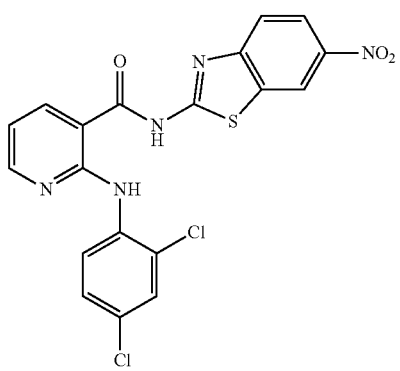
7
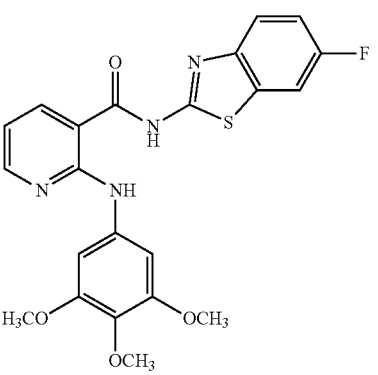
11
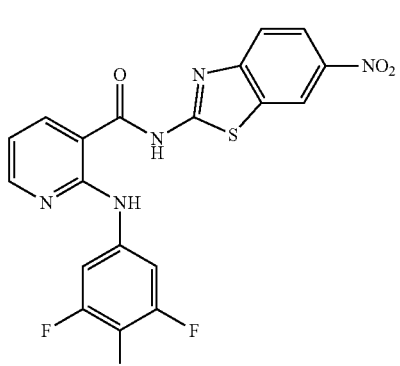
8
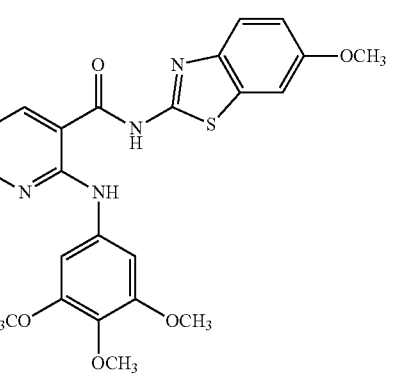
12
In yet another embodiment of the present invention, said compounds are useful as anticancer agents and apoptosis inducers.

The present invention provides a process for the preparation 2-anilino nicotinyl linked 2-amino benzothiazole conjugates of general formula A and the process comprising the steps of:

i. refluxing 2-chloro nicotinic acid ethyl ester (13) with substituted anilines (14-20) wherein $R^1$ represents hydrogen, chloro $R^2$ represents hydrogen, fluoro, chloro, methoxy, $R^3$ represents hydrogen, fluoro, chloro, methoxy and $R^4$ represents hydrogen, fluoro or methoxy

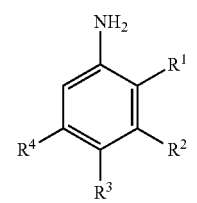

14-20

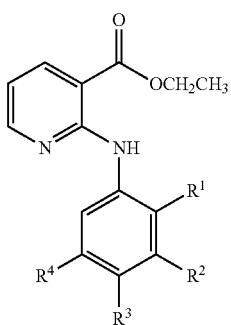

21-27 in organic solvent to give the coupled 2-anilino nicotinic acid esters (21-27);

ii. treating 2-anilino nicotinic acid esters (21-27) as obtained in step (i) with 2N NaOH solution in organic solvent to obtain sodium salt of 2-anilino nicotinic acid which on treatment with 2N HCl form 2-anilino nicotinic acids (28-34) wherein $R^1$ represents hydrogen, chloro, $R^2$ represents hydrogen, fluoro, chloro, methoxy, $R^3$ represents hydrogen, fluoro, chloro, methoxy and $R^4$ represents hydrogen, fluoro, methoxy;

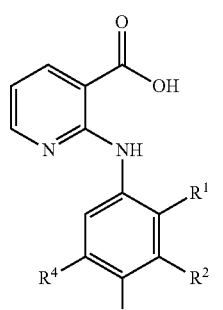

28-34

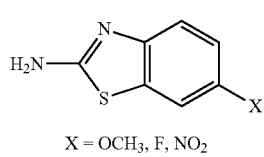

35-37

X = OCH₃, F, NO₂ iii. treating 2-anilino nicotinic acids (28-34) as obtained in step (ii) and 6-substituted 2-amino benzothiazoles (35-37) with EDCI/HOBt in dry DMF to obtain compounds of general formula A (4-12).

In yet another embodiment of the present invention, organic solvent used in step (i) is ethylene glycol.

In yet another embodiment of the present invention, organic solvent used in step (ii) is selected from methanol and ethanol.

In yet another embodiment of the present invention, 2-anilino nicotinyl linked 2-amino benzothiazole conjugates of formula 4-8 exhibiting an in vitro anticancer activity against the eleven human cancer cell lines Neuroblastoma cancer cell line (IMR-32), Cervical cancer cell line (Hela), Colon cancer cell lines (Sw-620, HCT-15), Prostate cancer cell lines (DU-145, PC-3), Lung cancer cell line (A549), Liver cancer cell line (Hep-2), Ovary cancer cell lines (OVCAR-5, IGR-OV-1), Breast cancer cell line (MCF-7) at 1 µM concentration.

In yet another embodiment of the present invention, percentage of growth inhibition are 50% for compound 4 in HEP-2, 53 and 53% for compound 5 in IMR-32, DU-145, 53% for compound 6 in HEP-2, 80% for compound 7 in MCF-7 and 58% for compound 8 in DU-145 at an exposure period of at least 48 hrs at 1 µM concentration.

In yet another embodiment of the present invention, 2-anilino nicotinyl linked 2-amino benzothiazole conjugates of formula 4-8 exhibiting an in vitro anticancer activity against ten human cancer cell lines selected from the group consisting of neuroblastoma cancer cell lines (IMR-32, SK—NS—H), cervical cancer cell line (SiHa), colon cancer cell lines (Sw-620, HCT-15, 502713), prostate cancer cell line (DU-145), lung cancer cell line (A549), liver cancer cell line (Hep-2) and ovary cancer cell line (OVCAR-5) at 10 µM concentration.

In yet another embodiment of the present invention, percentage of growth inhibition of 2-anilino nicotinyl linked 2-amino benzothiazole conjugates of formula 4-8 for two neuroblastoma human cancer cell lines (IMR-32, SK—NS—H) are in the range of 45 to 48, 55 to 64, 33 to 63, 48 to 50, 49 to 72% respectively at an exposure period of at least 48 hrs at 10 µM concentration.

In yet another embodiment of the present invention, percentage of growth inhibition of 2-anilino nicotinyl linked 2-amino benzothiazole conjugates of formula 4-8 for one cervical human cancer cell line (SiHa) are 53, 66, 23, 35, 70% respectively at an exposure period of at least 48 hrs at 10 µM concentration.

In yet another embodiment of the present invention, percentage of growth inhibition of 2-anilino nicotinyl linked 2-amino benzothiazole conjugates of formula 4-8 for three colon human cancer cell lines (SW-620, HCT-15, 502713) are in the range of 63 to 66, 47 to 64, 55 to 67, 2 to 75, 62 to 80% respectively at an exposure period of at least 48 hrs at 10 µM concentration.

In yet another embodiment of the present invention, percentage of growth inhibition of 2-anilino nicotinyl linked 2-amino benzothiazole conjugates of formula 4-8 for one prostate human cancer cell line (DU-145) are 52, 32, 51, 39 and 39% respectively at an exposure period of at least 48 hrs at 10 µM concentration.

In yet another embodiment of the present invention, percentage of growth inhibition of 2-anilino nicotinyl linked 2-amino benzothiazole conjugates of formula 4-8 for one lung human cancer cell line (A549) are 31, 3, 18, 19 and 27% respectively at an exposure period of at least 48 hrs at 10 µM concentration.

In yet another embodiment of the present invention, percentage of growth inhibition of 2-anilino nicotinyl linked 2-amino benzothiazole conjugates of formula 4-8 for one liver human cancer cell line (Hep-2) are 26, 5, 52, 14, and 0% respectively at an exposure period of at least 48 hrs at 10 µM concentration.

In yet another embodiment of the present invention, percentage of growth inhibition of 2-anilino nicotinyl linked 2-amino benzothiazole conjugates of formula 4-8 for one ovary human cancer cell line (OVCAR-5) are 50, 52, 53, 0 and 52% respectively at an exposure period of at least 48 hrs at 10 µM concentration.

In yet another embodiment of the present invention, 2-anilino nicotinyl linked 2-amino benzothiazole conjugates of formula 9-12 exhibiting an in vitro anticancer activity against fifty nine human cancer cell lines, derived from nine cancer types selected from the group consisting of leukemia cancer cell lines, non small cell lung cancer cell lines, colon cancer cell lines, CNS cancer cell lines, renal cancer cell lines, prostate cancer cell lines, ovarian cancer cell lines, breast cancer cell lines and melanoma cancer cell lines.

In yet another embodiment of the present invention, 2-anilino nicotinyl linked 2-amino benzothiazole conjugates of formula 9-12 exhibiting an in vitro anticancer activity against six leukemia cancer cell lines (CCRF-CEM, HL-60, K-562, MOLT-4, SR and RPMI-8226) for $GI_{50}$ are in the range of 0.726 to 2.28, 1.78 to 3.03, 1.68 to 3.26, 8.91 to 32.3 µM respectively at an exposure period of at least 48 hrs.

In yet another embodiment of the present invention, 2-anilino nicotinyl linked 2-amino benzothiazole conjugates of formula 9-12 exhibiting an in vitro anticancer activity against nine Non-small cell lung cancer cell lines (A549/ATCC, EKVX, HOP-62, HOP-92, NCI-H226, NCI-H23, NCI-H322M, NCI-H460 and NCI-H522) for $GI_{50}$ are in the range of 1.02 to 3.25, 1.48 to 3.94, 1.48 to 5.78, 2.60 to 17.3 µM respectively at an exposure period of at least 48 hrs.

In yet another embodiment of the present invention, 2-anilino nicotinyl linked 2-amino benzothiazole conjugates of formula 9-12 exhibiting an in vitro anticancer activity against seven colon cancer cell lines (COLO 205, HCC-2998, HCT-116, HCT-15, HT29, KM12 and SW-620) for $GI_{50}$ are in the range of 1.02 to 3.32, 1.90 to 3.74, 2.94 to 5.15, 4.50 to 17.7 µM respectively at an exposure period of at least 48 hrs.

In yet another embodiment of the present invention, 2-anilino nicotinyl linked 2-amino benzothiazole conjugates of formula 9-12 exhibiting an in vitro anticancer activity against six CNS cancer cell lines (SF-268, SF-295, SF-539, SNB-19, SNB-75 and U251) for $GI_{50}$ are in the range of 1.80 to 3.93, 1.83 to 4.02, 2.55 to 6.56, 2.81 to 15.0 µM respectively at an exposure period of at least 48 hrs.

In yet another embodiment of the present invention, 2-anilino nicotinyl linked 2-amino benzothiazole conjugates of formula 9-12 exhibiting an in vitro anticancer activity against seven ovarian cancer cell lines (IGROV-1, OVCAR-3, OVCAR-4, OVCAR-5, OVCAR-8, NCI/ADR-RES and SK-OV-3) for $GI_{50}$ are in the range of 2.00 to 2.92, 1.82 to 4.46, 1.77 to 25.6, 3.72 to 15.0 µM respectively at an exposure period of at least 48 hrs.

In yet another embodiment of the present invention, 2-anilino nicotinyl linked 2-amino benzothiazole conjugates of formula 9-12 exhibiting an in vitro anticancer activity against seven renal cancer cell line (A498, 786-0, ACHN, CAKI-1, SN12C, TK-10 and UO-31) for $GI_{50}$ are in the range of 1.94 to 3.08, 1.10 to 3.77, 3.15 to 5.51, 2.19 to 16.4 µM respectively at an exposure period of at least 48 hrs.

In yet another embodiment of the present invention, 2-anilino nicotinyl linked 2-amino benzothiazole conjugates of formula 9-12 exhibiting an in vitro anticancer activity against two prostate cancer cell lines (PC-3, DU-145) for $GI_{50}$ are in the range of 2.13 to 3.67, 2.11 to 3.53, 2.73 to 5.50, 6.67 to 14.6 µM respectively at an exposure period of at least 48 hrs.

In yet another embodiment of the present invention, 2-anilino nicotinyl linked 2-amino benzothiazoles conjugates of formula 9-12 exhibiting an in vitro anticancer activity against six breast cancer cell line (MCF7, MDA-MB-231/ATCC, HS 578T, BT-549, TD-47D and MDA-MB-468) for $GI_{50}$ are in the range of 0.73 to 2.38, 1.88 to 3.41, 1.22 to 4.61, 0.51 to 17.8 µM respectively at an exposure period of at least 48 hrs.

In yet another embodiment of the present invention, 2-anilino nicotinyl linked 2-amino benzothiazole conjugates of formula 9-12 exhibiting an in vitro anticancer activity against nine melanoma cancer cell lines (LOX IMVI, MALME-3M, M14, MDA-MB-435, SK-MEL-2, SK-MEL-28, SK-MEL-5, UACC-257 and UACC-62) for $GI_{50}$ are in the range of 0.164 to 3.51, 0.17 to 4.19, 1.63 to 4.33, 1.85 to 15.7 µM respectively at an exposure period of at least 48 hrs.

In yet another embodiment of the present invention, 2-anilino nicotinyl linked 2-amino benzothiazole conjugates of formula 4-8 exhibiting inhibition of cell proliferation ($IC_{50}$) in different human cancer cell lines selected from the group consisting of leukemia cancer cell line (HL-60), cervical cancer cell lines (SiHa, HeLa) cells, breast cancer cell line (MCF-7) and colon cancer cell line (HCT-15).

In yet another embodiment of the present invention, 2-anilino nicotinyl linked 2-amino benzothiazole conjugates of formula 4-8 are cytotoxic in human leukemia cancer cell line (HL-60) and their $IC_{50}$ value is in the range from 0.08 to 0.7 µM.

In yet another embodiment of the present invention, 2-anilino nicotinyl linked 2-amino benzothiazole conjugates of formula 6, wherein $IC_{50}$ values for cervical cancer cell lines (SiHa and HeLa) are 7 and 8 µA4 respectively.

In yet another embodiment of the present invention, 2-anilino nicotinyl linked 2-amino benzothiazole conjugates of formula 4-8 exhibiting ratio of $IC_{50}$ value between normal (monkey kidney CV-1 cells) to cancer cell lines (CV-1/HL-60) is in the range from 2-1250 times.

In yet another embodiment of the present invention, 2-anilino nicotinyl linked 2-amino benzothiazole conjugates of formula 4-8 induce DNA fragmentation in leukemia HL-60 cancer cell cells at 1 µM.

In yet another embodiment of the present invention, 2-anilino nicotinyl linked 2-amino benzothiazole conjugates of formula 4-8 induce the apoptosis, analyzed by flow cytometric analysis preferably compound 8 has the highest apoptotic potential in HL-60 cells showing around 70% cells apoptotic.

In yet another embodiment of the present invention, 2-anilino nicotinyl linked 2-amino benzothiazole conjugates of formula 4-8 exhibiting continuous increase in sub-G0 fraction implying the extent of cell death preferably compound 6 and 8 are showing 60% and 90% DNA damage respectively in HL-60 cancer cell line.

In yet another embodiment of the present invention, 2-anilino nicotinyl linked 2-amino benzothiazole conjugates of formula 4-8 exhibiting intracellular peroxide reactive oxygen species (ROS) generation in HL-60 cells by DCFH-DA by using flow cytometry preferably compound 5, 4 and 6 show significant increase of ~44, 31 and 16% in DCF positive cell population in HL-60 cells.

In yet another embodiment of the present invention, 2-anilino nicotinyl linked 2-amino benzothiazole conjugates of formula 4-8 exhibiting no nitric oxide induction in HL-60 cells for 24 h at 1 µM.

In yet another embodiment of the present invention, 2-anilino nicotinyl linked 2-amino benzothiazole conjugates of formula 4-8 inducing loss of mitochondrial membrane potential preferably compound 4, 6-8 induce loss of mitochondria membrane potential in HL-60 cells in which 8 have highest potential 45% loss in HL-60 cells for 48 h at 1 µM.

In yet another embodiment of the present invention, 2-anilino nicotinyl linked 2-amino benzothiazole conjugates of formula 4-8 exhibiting caspases activities viz. caspase-3, -8, and -9 in leukemia cells at 1 µM for 24 h preferably compound 8 for 24 h activated caspase-3,-8,-9 activities by 2-3 folds.

In yet another embodiment of the present invention, 2-anilino nicotinyl linked 2-amino benzothiazole conjugates of formula 4-8 inhibiting the expression of NF-kB preferably compound 8 significantly inhibit the expression of NF-kB in HL-60 cells.

In yet another embodiment of the present invention, 2-anilino nicotinyl linked 2-amino benzothiazole conjugates of formula 4-8 inhibiting the survivin levels preferably compound 6.

In yet another embodiment of the present invention, 2-anilino nicotinyl linked 2-amino benzothiazole conjugates of formula 4-8 inducing the PARP cleavage in HL-60 cells preferably compound 8.

In yet another embodiment of the present invention, 2-anilino nicotinyl linked 2-amino benzothiazole conjugates of formula 4-8 inhibit the expression of heat shock protein like HSP-90 preferably in HL-60 cells.

In yet another embodiment of the present invention, 2-anilino nicotinyl linked 2-amino benzothiazole conjugates of formula 4-8 not inhibits the Bcl-2 level in HL-60 cells as evident by the loss of mitochondrial membrane potential.

In yet another embodiment of the present invention, 2-anilino nicotinyl linked 2-amino benzothiazole conjugates of formula 4-8 inhibit topoisomerase II preferably 4-5, 7-8 showed more potent effect relative to etoposide on DNA relaxation induced by topoisomerase in presence of these compounds at 1 µM concentration more preferably compound 8 inhibits maximum inhibition.

In yet another embodiment of the present invention, 2-anilino nicotinyl linked 2-amino benzothiazole conjugates of formula 4-8 exhibiting an in vivo anticancer activity against the Ehrlich Ascites Carcinoma (EAC) and evaluation of tumor growth, percent tumor growth inhibition was calculated based on the total number of tumor cells present in the peritoneal cavity as on day 12 of the experiment.

In yet another embodiment of the present invention, 2-anilino nicotinyl linked 2-amino benzothiazole conjugates of formula 4 was found to be toxic at 50 mg/Kg dose exhibiting 42.21% anticancer activity against EAC at 10 mg/Kg dose level.

In yet another embodiment of the present invention, 2-anilino nicotinyl linked 2-amino benzothiazole conjugates of formula 5 found to be toxic to animals at a dose of 30 mg/kg as all the seven animals in the group died during the course of 9 days treatment showing 20.90% anticancer activity against EAC at 5 mg/kg dose level.

In yet another embodiment of the present invention, 2-anilino nicotinyl linked 2-amino benzothiazole conjugates of formula 6 exhibiting 22.18, 43.11 and 68.11% anticancer activity against EAC at 20, 30 and 40 mg/kg dose level showing maximum activity of 68.11% accompanied by considerable toxicity to animals.

In yet another embodiment of the present invention, 2-anilino nicotinyl linked 2-amino benzothiazole conjugates of formula 8 exhibiting 53.15% anticancer activity against EAC at 0.3 mg/kg dose level.

In yet another embodiment of the present invention, a pharmaceutical composition comprising 2-anilino nicotinyl linked 2-amino benzothiazole hybrids, its derivatives, analogues, salts or mixture thereof optionally with pharmaceutically acceptable carriers, adjuvants and additives of formula A as potential anti cancer agents and apoptosis inducers.

DETAILED DESCRIPTION OF THE INVENTION

Figure 1A:
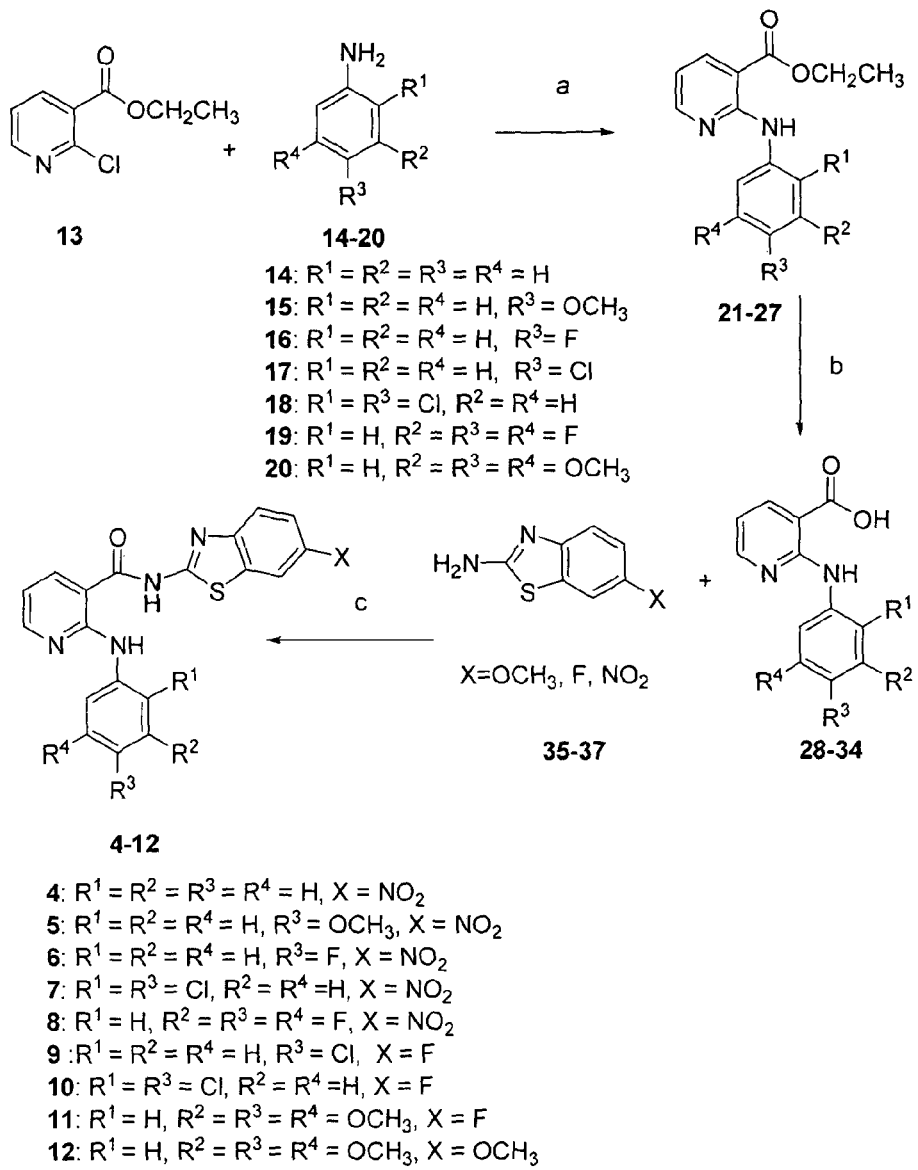
FIG. 1A shows process steps for the preparation of compound 4-12. Wherein reagent and conditions are (a) ethylene glycol, 160° C., 6 h; (b)$_2$N NaOH, ethanol reflux, 2 h; (c)EDCl/HOBt, dry DMF, 0° C., 30 min the n rt, 8-10 h.
Figure 1B:
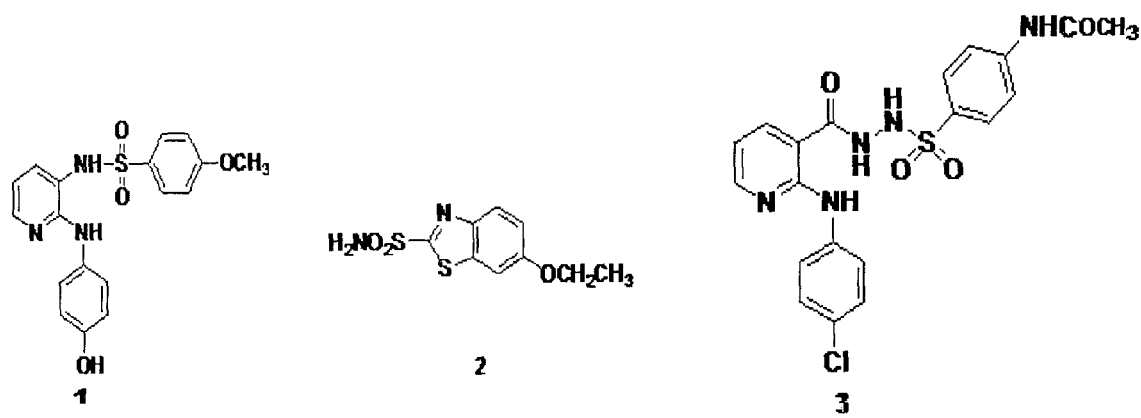
FIG. 1B shows chemical structures of E7010 (1), ethoxazolamide (2) and 2-anilino substituted nicotinyl arylsulfonylhydrazide (3)

2-Anilino nicotinyl linked 2-amino benzothiazole conjugates have shown promising anticancer activity in various cell lines. The compounds synthesized are of immense biological significance and known to be apoptosis inducers. This resulted in design and synthesis of new congeners as illustrated in FIG. 1A, which comprise:

i. The 2-chloro nicotinic acid ethyl ester (13) was refluxed with substituted anilines (14-20) in ethylene glycol at a temperature in the range of 150 to 160° C. for time period in the range of 5-6 hours ii. 2-anilino nicotinic acid esters (21-27) reflux with 2N NaOH solution in ethanol for 2 hrs to obtain sodium salt of 2-anilino nicotinic acid which on treatment with 2N HCl to form 2-anilino nicotinic acids (28-34).

iii. The synthesis of 2-anilino nicotinyl linked amino benzothiazoles hybrids (4-12) as anticancer and apoptosis inducers were carried out by the reaction of 2-anilino nicotinic acids (28-34) and 6-substituted 2-amino benzothiazoles (35-37) with EDCI/HOBt in dry DMF. (FIG. 1A).

iv. Purification by column chromatography using different solvents like ethyl acetate, hexane, chloroform and methanol.

Invention provides 2-anilino nicotinyl linked 2-amino benzothiazole conjugates of formula 4-8. Effect of these compounds on different cell death targets in HL-60 cells treated with tested compounds at 1 µM for 24 h and expression of key apoptotic proteins like nuclear factor kappa B (NF-kB), survivin; Poly ADP Ribose polymerase (PARP), Bcl-2 and heat shock protein (HSP-90) were analyzed through western blot. Compound 8 significantly inhibit the expression of NF-kB in HL-60 cells whereas rests of the compounds have no effect on NF-kB level. Almost all the tested compounds (4-8) inhibit the survivin level, but 6 have highest inhibition potential among them. All the tested compounds induce the PARP cleavage, compound 8 has the highest potential among them in HL-60 cells. Inspite of NF-kB, survivin, PARP some of the compounds (5-7) significantly inhibit the expression of heat shock protein like HSP-90 in HL-60. Cancer cells have very high level of heat shock proteins. Interestingly, no tested compounds inhibit the Bcl-2 level in HL-60 cells as evident by the loss of mitochondrial membrane potential by some of the molecules.

EXAMPLES

Following examples are given by way of illustration and therefore should not be construed to limit the scope of the present invention in any manner.

Example 1

N-3-(6-Nitro-1,3-benzothiazol-2-yl)-2-(phenylamino)-3-pyridinecarboxamide (4)

Compound 13 (185 mg, 1 mmol) and aniline (14, 93 mg, 1 mmol) was taken in ethylene glycol and refluxed at 160° C. for 6 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain Ethyl 2-(anilino) nicotinate (21) as pure product. Ethyl 2-(anilino) nicotinate (21, 242 mg, 1 mmol) were refluxed with 2N NaOH in ethanol for 2 h. The reaction mixture was cooled and left acidified with 2N HCl white solids obtained, filtered and washed with water to give pure compound of 2-(phenyl amino) nicotinic acid (28). To a stirred solution of 2-(phenyl amino) nicotinic acid (28, 214 mg, 1 mmol) in dry DMF (10 mL) hydroxy benzotriazole (HOBt) (1.2 mmol) were added at 0° C. After 10 min 1-ethyl-3-(3-dimethylaminopropyl) carbodiimide (EDCI) (1.2 mmol) was added and finally 2-amino-6-nitro benzothiazole (37, 137 mg, 0.7 mmol) were added. Resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (4) was purified by column chromatography employing EtOAc/hexane as an eluent.

Mp 235-237° C.; $^1$H NMR (200 MHz, CDCl$_3$+DMSO-d$_6$) δ 10.52 (s, 1H), 8.77 (d, J=2.2 Hz, 1H), 8.50 (dd, J=7.9, 1.4 Hz, 1H), 8.37 (dd, J=5.0, 2.2 Hz, 1H), 8.27 (dd, J=9.3, 2.2 Hz, 2H), 7.85-7.67 (m, 2H), 7.32 (t, J=8.6 Hz, 2H), 7.03 (t, J=7.2, 1H), 6.86-6.74 (m, 1H); LRMS (ESI, m/z) 392 [(M+H)$^+$].; IR(KBr) ($v_{max}$/cm$^{-1}$): 3376 (NH), 2925, 1653 (C=O), 1519, 1444, 1305, 1259, 1121.

Example 2

N3-(6-nitro-1,3-benzothiazol-2-yl)-2-(4-methoxyanilino)nicotinamide (5)

Compound 13 (185 mg, 1 mmol) and 4-methoxy aniline (15, 123 mg, 1 mmol) was taken in ethylene glycol and refluxed at 150° C. for 5 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain ethyl-2-(4-methoxy anilino) nicotinate (22) as pure product. Ethyl 2-(4-methoxy anilino) nicotinate (22, 272 mg 1 mmol) were refluxed with 2N NaOH in ethanol for 2 h. The reaction mixture was cooled and left acidified with 2N HCl white solids obtained, filtered and washed with water to give pure compound of 2-(4-methoxyphenylamino)nicotinic acid (29).

To a stirred solution of 2-(4-methoxy phenylamino)nicotinic acid (29, 244 mg 1 mmol) in dry DMF (10 mL) hydroxy benzotriazole HOBt (1.2 mmol) were added at 0° C. After 10 min 1-ethyl-3-(3-dimethylaminopropyl) carbodiimide (EDCI) (1.2 mmol) was added and finally 2-amino-6-nitrobenzothiazole (37, 137 mg, 0.7 mmol) were added, then the resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (5) was purified by column chromatography employing EtOAc/Hexane as an eluent.

Mp 249-252° C.; $^1$H NMR (200 MHz, CDCl$_3$+DMSO-d$_6$) δ 13.0 (bs, 1H), 10.36 (s, 1H), 8.81 (s, 1H), 8.52 (d, J=7.1 Hz, 1H), 8.36-8.24 (m, 2H), 7.81 (d, J=9.5 Hz, 1H), 7.56 (d, J=8.7 Hz, 2H), 6.85 (d, J=9.5 Hz, 2H), 6.78-6.69 (m, 1H), 3.77 (s, 311); LRMS (ESI, m/z) 422 [(M+H)$^+$].; IR(KBr) ($v_{max}$/cm$^{-1}$): 3380 (NH), 2931, 1653 (C=O), 1620 (C—N), 1575, 1511, 1451, 1339, 1250.

Example 3

N3-(6-nitro-1,3-benzothiazol-2-yl)-2-(4-fluoroanilino)nicotinamide (6)

Compound 13 (185 mg, 1 mmol) and 4-fluoro aniline (16, 147 mg, 1 mmol) was taken in ethylene glycol and refluxed at 150° C. for 5 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain Ethyl 2-(4-fluoroanilino) nicotinate (23) as pure product. Ethyl 2-(4-fluoroanilino) nicotinate (23, 260 mg, 1 mmol) were refluxed with 2N NaOH in ethanol for 2 h. The reaction mixture was cooled and left acidified with 2N HCl white solids obtained, filtered and washed with water to give pure compound of 2-(4-fluoroanilino)nicotic acid (30). To a stirred solution of 2-(4-fluorophenylamino) nicotinic acid (30, 232 mg 1 mmol) in dry DMF (10 mL) hydroxy benzotriazole HOBt (1.2 mmol) were added at 0° C. After 10 min 1-ethyl-3-(3-dimethylaminopropyl) carbodiimide (EDCI) (1.2 mmol) was added and finally 2-amino 6-nitro benzothiazole 37 (137 mg, 0.7 mmol) were added, then the resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (6) was purified by column chromatography employing EtOAc/Hexane as an eluent.

Mp 232-234° C.; $^1$H NMR (200 MHz, CDCl$_3$+DMSO-d$_6$) δ 10.23 (s, 1H), 9.08 (d, J=2.9 Hz, 1H), 8.47 (dd, J=8.0, 1.5 Hz, 1H), 8.38 (dd, J=5.1, 2.2 Hz, 1H), 8.32 (dd, Jz=9.4, 2.9 Hz, 1H), 7.90 (d, J=5.1 Hz, 1H), 7.72 (dd, J=9.4, 5.1 Hz, 2H), 7.17 (t, J=9.4 Hz, 2H), 6.98-6.89 (m, 1H); LRMS (ESI, m/z) 410 [(M+H)$^+$].; IR(KBr) ($v_{max}$/cm$^{-1}$): 3377 (NH), 3060, 1654 (C=O), 1621 (C—N), 1587, 1508, 1450, 1340, 1217.

Example 4

N3-[6-(nitro-1,3-benzothiazol-2-yl]-2-[(2,4-dichlorophenyl)amino]-3-pyridine carboxamide (7)

Compound 13 (185 mg, 1 mmol) and 2,4-dichloro aniline (18, 92 mg, 1 mmol) was taken in ethylene glycol and refluxed at 160° C. for 6 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain Ethyl 2-(2,4-dichloro anilino) nicotinate (25) as pure product. Ethyl 2-(2,4-dichloro anilino) nicotinate (25, 311 mg, 1 mmol) were refluxed with 2N NaOH in ethanol for 2 h. The reaction mixture was cooled and left acidified with 2N HCl white solids obtained, filtered and washed with water to give pure compound of 2-(2,4-dichlorophenylamino) nicotinic acid (32). To a stirred solution of 2-(2,4-dichlorophenylamino)nicotinic acid (32, 283 mg, 1 mmol) in dry DMF (10 mL) hydroxy benzotriazole HOBt (1.2 mmol) were added at 0° C. After 10 min 1-ethyl-3-(3-dimethylaminopropyl) carbodiimide (EDCI) (1.2 mmol) was added and finally 2-amino 6-nitro benzothiazole (37, 137 mg, 0.7 mmol) were added, then the resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (7) was purified by column chromatography employing EtOAc/Hexane as an eluent.

Mp 236-237° C.; $^1$H NMR (200 MHz, CDCl$_3$+DMSO-d$_6$) δ 10.93 (s, 1H), 8.85 (d, J=2.2 Hz, 1H), 8.66 (d, J=8.8 Hz, 1H), 8.60 (dd, J=8.0, 1.5 Hz, 1H), 8.39 (dd, J=5.1, 1.5 Hz, 1H), 8.26 (dd, J=9.5, 2.2 Hz, 1H), 7.84 (t, J=8.8 Hz, 1H), 7.42 (d, J=2.2 Hz, 1H), 7.22 (dd, J=8.8, 2.2 Hz, 1H), 6.99-6.89 (m, 1H); LRMS (ESI, m/z) 460 [(M)$^+$].; IR(KBr) ($v_{max}$/cm$^{-1}$): 3333 (NH), 1660 (C=O), 1615 (C—N), 1523, 1340, 1283, 757.

Example 5

N3-(6-nitro-1,3-benzothiazol-2-yl)-2-[(3,4,5-trifluorophenyl)amino]-3-pyridine carboxamide (8)

Compound 13 (185 mg, 1 mmol) and 3,4,5-trifluoro aniline (19, 147 mg, 1 mmol) was taken in ethylene glycol and refluxed at 150° C. for 5 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain Ethyl 2-(3,4,5 trifluoroanilino) nicotinate (26) as pure product. Ethyl 2-(3, 4,5 trifluoroanilino) nicotinate (26, 296 mg, 1 mmol) were refluxed with 2N NaOH in ethanol for 2 h. The reaction mixture was cooled and left acidified with 2N HCl white solids obtained, filtered and washed with water to give pure compound of 2-(3,4,5-trifluorophenylamino) nicotinic acid (33). To a stirred solution of 2-(3,4,5-trifluorophenylamino) nicotinic acid (33, 252 mg, 1 mmol) in dry DMF (10 mL) hydroxy benzotriazole HOBt (1.2 mmol) were added at 0° C. After 10 min 1-ethyl-3-(3-dimethylaminopropyl) carbodiimide (EDCI) (1.2 mmol) was added and finally 2-amino 6-nitro benzothiazole (37, 137 mg, 0.7 mmol) were added, then the resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (8) was purified by column chromatography employing EtOAc/Hexane as an eluent.

Mp 233-237° C.; $^1$H NMR (500 MHz, CDCl$_3$+Acetone-d$_6$) δ 10.71 (bs, 1H), 8.86 (d, J=2.9 Hz, 1H), 8.64 (d, J=6.8 Hz, 1H), 8.49 (dd, J=4.9, 1.9 Hz, 1H), 8.32 (dd, J=8.8, 1.9 Hz, 1H), 7.86 (d, J=8.8 Hz, 1H), 7.68-7.61 (m, 2H), 6.99 (dd, J=7.8, 4.9 Hz, 1H); LRMS (ESI, m/z) 446 [(M+H)$^+$].; IR(KBr) ($v_{max}$/cm$^{-1}$): 3322 (NH), 3100, 2928, 1659 (C=O), 1524, 1441, 1341, 1284, 1135, 1044.

Example 6

N3-(6-fluoro-1,3-benzothiazol-2-yl)-2-(4-chloroanilino)nicotinamide (9)

Compound 13 (185 mg, 1 mmol) and, 4-chloro aniline (17, 128 mg, 1 mmol) was taken in ethylene glycol and refluxed at 160° C. for 5 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain ethyl 2-(4-chloro anilino) nicotinate (24) as pure product. Ethyl 2-(4-chloro anilino) nicotinate (24, 276 mg, 1 mmol) were refluxed with 2N NaOH in ethanol for 2 h. The reaction mixture was cooled and left acidified with 2N HCl white solids obtained, filtered and washed with water to give pure compound of 2-(4-chlorophenylamino)nicotinic acid (31). To a stirred solution of 2-(4-chlorophenylamino) nicotinic acid (31, 249 mg, 1 mmol) in dry DMF (10 mL) hydroxy benzotriazole HOBt (1.2 mmol) were added at 0° C. After 10 min 1-ethyl-3-(3-dimethylaminopropyl) carbodiimide (EDCI) (1.2 mmol) was added and finally 2-amino 6-fluoro benzothiazole (36, 118 mg, 0.7 mmol) were added Then the resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (9) was purified by column chromatography employing EtOAc/Hexane as an eluent.

Mp 254-257° C.; $^1$H NMR (300 MHz, CDCl$_3$+DMSO-d$_6$) δ 10.66 (bs, 1H), 8.56 (dd, J=7.7, 1.3 Hz, 1H), 8.36 (dd, J=4.3, 1.1 Hz, 1H), 7.74 (d, J=8.9 Hz, 2H), 7.70 (t, J=4.5 Hz, 1H), 7.62 (dd, J=8.3, 2.4 Hz, 1H), 7.30 (d, J=8.7 Hz, 2H), 7.20 (dt, J=8.9, 2.3 Hz, 1H), 6.91-6.83 (m, 1H); LRMS (ESI, m/z) 399

[(M)$^+$].; IR(KBr) ($v_{max}$/cm$^{-1}$): 3421 (NH), 2924, 2854, 1656 (C=O), 1528, 1455, 1287, 1241, 1137, 762.

Example 7

N3-(6-fluoro-1,3-benzothiazol-2-yl)-2-(2,4-dichloroanilino)nicotinamide (10)

Compound 13 (185 mg, 1 mmol) and 2,4-dichloro aniline (18, 92 mg, 1 mmol) was taken in ethylene glycol and refluxed at 160° C. for 5 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain Ethyl. 2-(2,4-dichloro anilino) nicotinate (25) as pure product. Ethyl 2-(2,4-dichloro anilino) nicotinate (25, 311 mg, 1 mmol) were refluxed with 2N NaOH in ethanol for 2 h. The reaction mixture was cooled and left acidified with 2N HCl white solids obtained, filtered and washed with water to give pure compound of 2-(2,4-dichlorophenylamino)nicotinic acid (32). To a stirred solution of 2-(2,4-dichlorophenylamino)nicotinic acid (32, 283 mg, 1 mmol) in dry DMF (10 mL) hydroxy benzotriazole HOBt (1.2 mmol) were added at 0° C. After 10 min 1-ethyl-3-(3-dimethylaminopropyl) carbodiimide (EDCI) (1.2 mmol) was added and finally 2-amino 6-fluoro benzothiazole (36, 117 mg, 0.7 mmol) were added Then the resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (10) was purified by column chromatography employing EtOAc/hexane as an eluent.

Mp 208-210° C.; $^1$H NMR (500 MHz, Acetone-d$_6$) δ 11.76 (bs, 1H), 11.03 (s, 1H), 8.84 (dd, J=8.8, 3.9 Hz, 1H), 8.68 (dd, J=7.8, 2.0 Hz, 1H), 8.48 (d, J=3.9 Hz, 1H), 7.83 (dd, J=7.8, 2.9 Hz, 1H), 7.77 (dd, J=8.8, 3.9 Hz, 1H), 7.55 (d, J=2.9 Hz, 1H), 7.36 (dd, J=8.8, 2.9 Hz, 1H), 7.27 (dt, J=9.8, 2.9 Hz, 1H), 7.05 (dd, J=7.8, 4.9 Hz, 1H); LRMS (ESI, m/z) 433 [(M)$^+$].; IR(KBr) ($v_{max}$/cm$^{-1}$): 3173 (NH), 2923, 1666 (C=O), 1603 (C—N), 1551, 1517, 1462, 1300, 1251, 837, 765.

Example 8

N3-(6-fluoro-1,3-benzothiazol-2-yl)-2-(3,4,5-trimethoxyanilino)nicotinamide (11)

Compound 13 (185 mg, 1 mmol) and 3,4,5-methoxy aniline (20, 183 mg, 1 mmol) was taken in ethylene glycol and refluxed at 160° C. for 6 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain Ethyl 2-(3,4,5-trimethoxy anilino) nicotinate (27) as pure product. Ethyl2-(3,4,5-trimethoxy anilino) nicotinate (27, 332 mg, 1 mmol) were refluxed with 2N NaOH in ethanol for 2 h. The reaction mixture was cooled and left acidified with 2N HCl white solids obtained, filtered and washed with water to give pure compound of 2-(3,4,5-trimethoxyphenylamino) nicotinic acid (34). To a stirred solution of 2-(3,4,5-trimethoxyphenylamino) nicotinic acid (34, 244 mg, 1 mmol) in dry DMF (10 mL) hydroxy benzotriazole HOBt (1.2 mmol) were added at 0° C. After 10 min 1-ethyl-3-(3-dimethylaminopropyl) carbodiimide (EDCI) (1.2 mmol) was added and finally 2-amino 6-fluoro benzothiazole (36, 117 mg, 0.7 mmol) were added Then the resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (11) was purified by column chromatography employing EtOAc/Hexane as an eluent.

Mp 214-216° C. $^1$H NMR (200 MHz, CDCl$_3$+DMSO-d$_6$) δ 10.32 (s, 1H), 7.71-7.64 (m, 1H), 7.66 (q, J=4.5, 1.5 Hz, 1H), 7.56 (dd, J=7.6, 2.3 Hz, 1H), 7.55 (dd, J=8.3, 2.3 Hz, 1H), 7.21 (dt, J=9.1, 2.3 Hz, 1H), 7.01 (s, 2H), 6.86-6.79 (m, 1H), 3.92 (s, 6H), 3.87 (s, 3H); LRMS (ESI, m/z) 455 [(M+H)$^+$].; IR(KBr) ($v_{max}$/cm$^{-1}$): 3446 (NH), 3215, 3067, 2928, 2834, 1919, 1630 (C=O), 1604 (C—N), 1584, 1557, 1508, 1460, 1416, 1302, 1244, 1132.

Example 9

N-3-(6-methoxy-1,3-benzothiazol-2-yl)-2-(3,4,5-trimethoxyanilino) nicotinamide (12)

Compound 13 (185 mg, 1 mmol) and 3,4,5-methoxy aniline (20, 183 mg, 1 mmol) was taken in ethylene glycol and refluxed at 160° C. for 6 h. Then the reaction mixture was cooled and extracted in ethyl acetate (4×25 mL) from the aqueous layer and concentrated in vacuo. The compound was further purified by column chromatography using 60-120 silica gel (ethyl acetate/hexane, 1:9) to obtain Ethyl 2-(3,4,5-trimethoxy anilino) nicotinate (27) as pure product. Ethyl2-(3,4,5-trimethoxy anilino) nicotinate (27, 332 mg, 1 mmol) were refluxed with 2N NaOH in ethanol for 2 h. The reaction mixture was cooled and left acidified with 2N HCl white solids obtained, filtered and washed with water to give pure compound of 2-(3,4,5-trimethoxyphenylamino) nicotinic acid (34). To a stirred solution of 2-(3,4,5-trimethoxyphenylamino) nicotinic acid (34, 244 mg, 1 mmol) in dry DMF (10 mL) hydroxy benzotriazole HOBt (1.2 mmol) were added at 0° C. After 10 min 1-ethyl-3-(3-dimethylaminopropyl) carbodiimide (EDCI) (1.2 mmol) was added and finally 2-amino 6-methoxy benzothiazole (35, 126 mg, 0.7 mmol) were added Then the resulting mixture was stirred at room temperature (27° C.) for 8-10 h and then the reaction mixture was quenched with NaHCO$_3$ and extracted in ethyl acetate (4×25 mL) from the ice cold aqueous layer and dried over anhydrous Na$_2$SO$_4$. The resulting product (12) was purified by column chromatography employing EtOAc/hexane as an eluent.

Mp 121-125° C. Charred; $^1$H NMR (500 MHz, CDCl$_3$) δ 10.27 (s, 1H), 8.34 (d, J=2.9 Hz, 1H), 8.01 (d, J=6.8 Hz, 1H), 7.41 (d, J=8.7 Hz, 1H), 7.32 (s, 1H), 7.02 (s, 2H), 6.97 (d, J=8.7 Hz, 1H), 6.59-6.52 (m, 1H), 3.91 (s, 6H), 3.89 (s, 3H), 3.85 (s, 3H); LRMS (ESI, m/z) 467 [(M+H)$^+$].; IR(KBr) ($v_{max}$/cm$^{-1}$): 3454 (NH), 3221, 2931, 1603, 1512, 1468, 1316, 1262, 1133.

BIOLOGICAL ACTIVITY

Some of biological activity studies were carried out at the National Cancer Institute (NCI), Maryland, USA.

1. Biological activity of 2-anilino nicotinyl linked 2-amino benzothiazole conjugates In Vitro Cytotoxicity 2-Anilino nicotinyl linked 2-amino benzothiazoles conjugates of formula 4-8 have been tested against ten and eleven human cancer cell lines for 10 and 1 μM respectively derived from nine cancer types (leukemia, non-small cell lung cancer, colon cancer, CNS cancer, melanoma, ovarian cancer, renal cancer, prostate cancer and breast cancer) as per NCI protocol. For each compound, percentage of growth inhibition was calculated for individual cell lines at a minimum of two concentrations (1 and 10 μM). A protocol of 48 hrs continuous drug exposure was used, and a sulforhodamine B (SRB) protein assay was used to estimate cell viability or growth. The percentage of growth inhibition compared with the control was calculated in table 1 and table 2.

2-Anilino nicotinyl linked 2-amino benzothiazole conjugates of formula 9-12 were tested against fifty nine human cancer cell lines derived from nine cancer types (leukemia, non-small cell lung cancer, colon cancer, CNS cancer, melanoma, ovarian cancer, renal cancer, prostate cancer and breast cancer) as per NCI protocol. For each compound, dose response curves for individual cell lines were measured at a minimum of five concentrations at 10 fold dilutions. A protocol of 48 hrs continuous drug exposure was used, and a sulforhodamine B (SRB) protein assay was used to estimate cell viability or growth. The concentration for 50% cell growth inhibition ($GI_{50}$), compared with the control has been calculated in Table 3.

TABLE 1

Growth inhibition (%) for selected cancer cell lines of 2-anilino nicotinyl linked 2-amino benzothiazole conjugates of formula 4-8 at 10 μM

| Comp | IMR-32[f] | SK-NS-H[f] | SiHa[g] | Sw-620[h] | HCT-15[h] | 502713[h] | DU145[j] | A549[k] | HEP-2[l] | OVCAR-5[i] |
|---|---|---|---|---|---|---|---|---|---|---|
| 4 | 45 | 48 | 53 | 65 | 66 | 63 | 52 | 31 | 26 | 50 |
| 5 | 55 | 64 | 66 | 64 | 47 | 59 | 32 | 3 | 5 | 52 |
| 6 | 33 | 63 | 23 | 67 | 55 | 66 | 51 | 18 | 52 | 53 |
| 7 | 48 | 50 | 35 | 61 | 75 | 2 | 39 | 19 | 14 | 0 |
| 8 | 72 | 49 | 70 | 70 | 62 | 80 | 39 | 27 | 0 | 52 |
| Pac[b] | 46 | 20 | 49 | 73 | 37 | 59 | 42 | 41 | —[a] | 51 |
| 5-FU[c] | 71 | 7 | 44 | 76 | 44 | 21 | —[a] | —[a] | —[a] | 22 |
| Mito-c[d] | —[a] | —[a] | —[a] | —[a] | —[a] | —[a] | 44 | 34 | 7 | —[a] |

TABLE 2

Growth inhibition (%) for selected cancer cell line of 2-anilino nicotinyl linked 2-amino benzothiazoles conjugates of formula 4-8 at 1 μM

| Comp | IMR-32[f] | MCF-7[m] | Sw-620[hb] | HCT-15[h] | IGR-OV-1[i] | DU145[j] | A549[k] | HEP-2[l] | OVCAR-5[i] | PC-3[j] | Hela[g] |
|---|---|---|---|---|---|---|---|---|---|---|---|
| 4 | 35 | 44 | 9 | 6 | 29 | 35 | 23 | 50 | 29 | 22 | 9 |
| 5 | 53 | 25 | 15 | 9 | 27 | 53 | 27 | 38 | 31 | 21 | 7 |
| 6 | 31 | 39 | 9 | 22 | 25 | 31 | 27 | 53 | 27 | 26 | 40 |
| 7 | 42 | 80 | 12 | 4 | 24 | 36 | 15 | 46 | 19 | 27 | 0 |
| 8 | 48 | 46 | 29 | —[a] | 42 | 58 | 27 | 49 | 37 | 41 | —[a] |
| 5-Fu[c] | —[a] | —[a] | 44 | 46 | —[a] | —[a] | —[a] | —[a] | —[a] | —[a] | —[a] |
| Pac[b] | —[a] | —[a] | —[a] | —[a] | —[a] | 44 | 34 | —[a] | —[a] | —[a] | —[a] |
| Mito-c[d] | —[a] | —[a] | —[a] | 51 | 63 | —[a] | —[a] | —[a] | —[a] | —[a] | —[a] |
| ADR[e] | —[a] | —[a] | —[a] | —[a] | —[a] | —[a] | —[a] | —[a] | —[a] | —[a] | —[a] |

[a]Not tested;
[b]paclitaxel;
[c]5-fluorouracil;
[d]mitomycin;
[e]adriamycin;
[f]neuroblastoma;
[g]cervical;
[h]colon;
[i]ovary;
[j]prostate;
[k]lung;
[l]liver;
[m]breast cancer cell lines

TABLE 3

$GI_{50}$ values for selected compounds (9-12)

| Cancer panel/cell line | Growth Inhibition $GI_{50}$ (μM) | | | |
|---|---|---|---|---|
| | 9 | 10 | 11 | 12 |
| Leukemia | | | | |
| CCRF-CEM | 1.06 | 1.85 | 3.26 | 20.1 |
| HL-60(TB) | 1.74 | 1.83 | 1.86 | 32.3 |
| K-562 | 0.726 | 1.78 | 1.68 | 8.91 |
| MOLT-4 | 2.22 | 2.27 | 2.11 | 24.2 |
| SR | 2.28 | 3.03 | 2.97 | 2.31 |
| RPMI-8226 | —[a] | —[a] | —[a] | 9.94 |
| Non-small lung | | | | |
| A549/ATCC | 2.32 | 2.96 | 3.11 | 7.38 |
| EKVX | 1.94 | 2.07 | 2.70 | 11.5 |
| HOP-62 | 2.70 | 3.94 | 5.78 | 6.33 |
| HOP-92 | 1.69 | 1.48 | 1.48 | 2.24 |
| NCI-H226 | 2.32 | 2.70 | 2.95 | 10.7 |
| NCI-H23 | 1.67 | 2.34 | 2.27 | 5.38 |
| NCI-H322M | 3.25 | 3.24 | 3.71 | 17.3 |
| NCI-H460 | 1.97 | 2.56 | 3.30 | 7.42 |
| NCI-H522 | 1.02 | 1.48 | 1.55 | 2.60 |
| Colon | | | | |
| COLO 205 | 1.68 | 1.90 | 3.04 | 17.4 |
| HCC-2998 | 2.75 | 3.54 | 2.94 | 17.0 |
| HCT-116 | 1.67 | 2.19 | 3.49 | 4.50 |
| HCT-15 | 3.32 | 3.74 | 4.38 | 11.2 |
| HT29 | 2.86 | 2.98 | 5.15 | 17.7 |
| KM12 | 2.61 | 2.90 | 3.79 | 4.51 |
| SW-620 | 1.02 | 3.40 | —[a] | 11.8 |
| CNS | | | | |
| SF-268 | 3.93 | 3.88 | 6.56 | 4.43 |
| SF-295 | 1.80 | 1.83 | 2.55 | 8.34 |
| SF-539 | 2.70 | 4.02 | 3.84 | 2.81 |
| SNB-19 | 3.65 | 3.66 | 3.49 | 15.0 |
| SNB-75 | 2.95 | 2.55 | 4.48 | 2.89 |
| U251 | 3.03 | 2.90 | 3.01 | 7.10 |
| Ovarian | | | | |
| IGROV1 | 2.00 | 1.82 | 1.77 | 13.2 |
| OVCAR-3 | 2.17 | 2.44 | 2.77 | 8.92 |
| OVCAR-4 | 2.92 | 2.96 | 2.73 | 15.0 |
| OVCAR-5 | 2.63 | 4.46 | 25.6 | 14.5 |
| OVCAR-8 | 2.24 | 2.78 | 3.62 | 6.52 |
| NCI/ADR-RES | 2.09 | 2.51 | 2.92 | 8.97 |
| SK-OV-3 | 2.23 | 2.50 | 7.40 | 3.72 |
| Renal | | | | |
| 786-0 | 2.78 | 3.77 | 5.51 | 5.60 |
| A498 | 1.92 | 2.83 | 3.45 | 2.19 |
| ACHN | 3.08 | 3.72 | 4.82 | 6.47 |
| CAKI-1 | 2.89 | 1.50 | 3.15 | 16.4 |
| SN12C | 2.30 | 2.32 | 4.73 | 11.7 |
| TK-10 | 3.00 | 3.05 | — | 4.31 |
| UO-31 | 1.94 | 1.10 | 3.37 | 9.30 |
| Prostate | | | | |
| PC-3 | 2.13 | 2.11 | 2.73 | 6.67 |
| DU-145 | 3.67 | 3.53 | 5.50 | 14.6 |
| Breast | | | | |
| MCF7 | 2.38 | 3.07 | 3.23 | 0.51 |
| MDA-MB-231/ATCC | 1.85 | 3.41 | 4.61 | 5.62 |
| HS 578T | 1.99 | 3.25 | 2.57 | 5.77 |
| BT-549 | 2.05 | 3.01 | 2.63 | 11.6 |
| T-47D | 0.73 | 1.93 | 2.30 | 5.06 |
| MDA-MB-468 | 1.61 | 1.88 | 1.22 | 17.8 |
| Melanoma | | | | |
| LOX IMVI | 2.62 | 4.19 | 3.87 | 15.7 |
| MALME-3M | 1.94 | 2.38 | 3.27 | 10.1 |
| M14 | 2.64 | 3.37 | 3.08 | 10.5 |
| MDA-MB-435 | 2.99 | 3.03 | 2.87 | 1.85 |
| SK-MEL-2 | 1.25 | 1.74 | 2.34 | — |
| SK-MEL-28 | 3.51 | 4.09 | 4.33 | 7.88 |
| SK-MEL-5 | 1.11 | 1.71 | 1.63 | 11.3 |
| UACC-257 | 0.164 | 0.17 | — | 8.45 |
| UACC-62 | 1.94 | 2.12 | 1.71 | 8.45 |

[a]Not tested

2. Effect of Tested Molecules on the Inhibition of Cell Proliferation ($IC_{50}$) in Different Human Cancer Cells In order to determine the mode of action of cell death in cancer cells, first we explored the cytotoxic potential of different structural analogs of benzothiazoles on different human cancer cell lines. The compounds (4-8) were tested for their cell growth inhibition by MTT method at the indicated concentrations for 48 h. Most of these compounds found to be cytotoxic in human leukemia HL-60 cells and their $IC_{50}$ value ranges from 0.08 to 0.7 μM. These compounds have limited or no cytotoxicity to cervical cancer SiHa, HeLa cells, breast cancer MCF-7 cells and colon cancer HCT-15 cells. Only Compound 6 was found to active in cervical cancer SiHa and HeLa cells with $IC_{50}$ value of 7 and 8 μM respectively (Table 4)

TABLE 4

Summary of $IC_{50}$ (μM) value in different cells

| Compound No | HL-60 | SiHa | HeLa | MCF-7 | HCT-15 | CV-1 |
|---|---|---|---|---|---|---|
| 4 | 0.58 | 28 | >100 | >100 | >100 | 70 |
| 5 | 0.7 | 28 | >100 | >100 | >100 | 10 |
| 6 | 0.3 | 7 | 8 | >100 | >100 | 15 |
| 7 | 0.4 | >50 | >100 | >100 | >100 | 0.8 |
| 8 | 0.08 | 36 | >100 | >100 | >100 | >100 |

These compounds were also evaluated for their cytotoxic potential in normal cells and for these purpose their $IC_{50}$ value were also determine in normal monkey kidney CV-1 cells by using MTT method. The ratios of normal to cancer cells $IC_{50}$ value were ranges from 10-1000 times (Table 5). Compound no 8 have very high safety window as its $IC_{50}$ value in normal cells is 1250 time higher than cancer cells.

TABLE 5

Comparison of $IC_{50}$ value between normal and cancer cells

| Compound No | Normal/Cancer cell IC50 value comparision (CV-1/HL-60) |
|---|---|
| 4 | 120.68 |
| 5 | 14.2 |
| 6 | 50. |
| 7 | 2 |
| 8 | 1250 |

3. Flow Cytometric Analysis of Apoptosis and Necrosis Using Annexin VIM Dual Staining During apoptosis an important biochemical change that take place in cells undergoing is flipping of phosphatidyl serine lipid from the inner leaflet of the cellular membrane to the outer one.

Figure 2:
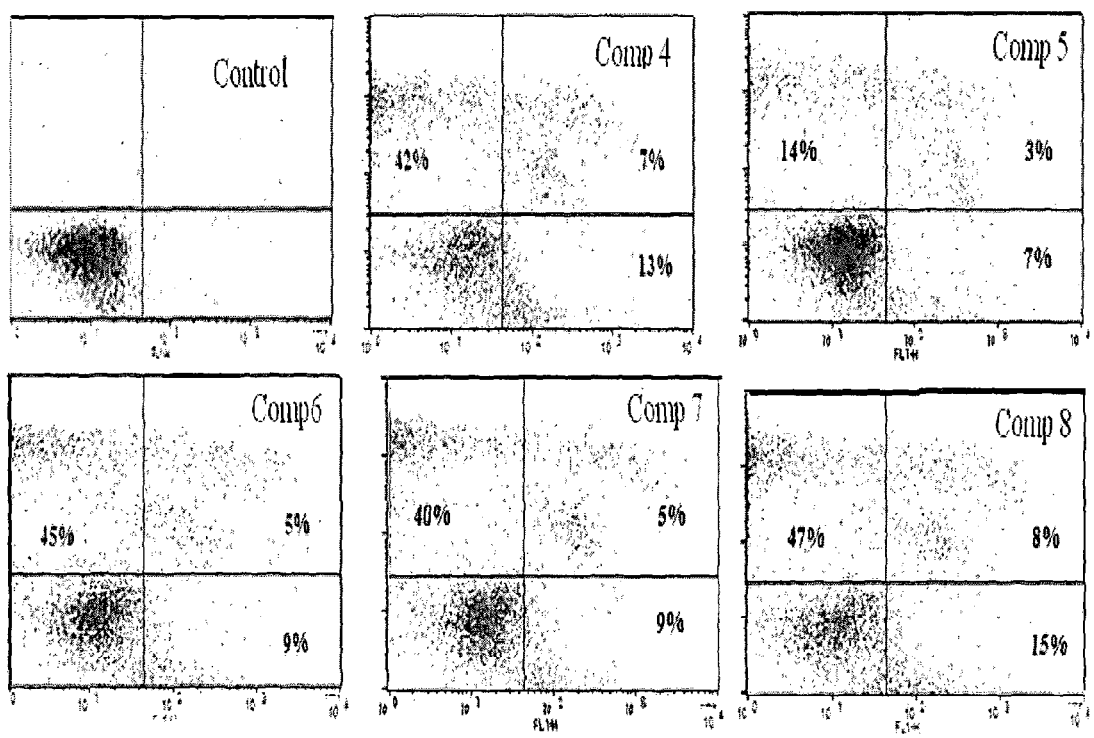
FIG. 2 shows Measurement of apoptosis and necrosis in HL-60 cells by Annexin-V-FITC method.

Annexin V a calcium dependent phospholipids binding protein has a high affinity for PS. Hence FITC-labeled Annexin V has been used in the flow cytometric detection to identify apoptotic cells. Compounds 4-8 at 1 µM were treated with HL-60 cells were incubated for 24 h and the extent of apoptosis vs. necrosis was analyzed from the quadrant analysis of cell population with Annexin V-FITC. Both the apoptotic and post apoptotic cell populations increased in HL-60 cells. All the compounds induce apoptosis where as compound 8 which showed highest apoptotic induction in HL-60 cells (around 70% cells are apoptotic) (FIG. 2).

4. Caspases Induction

Figure 3:
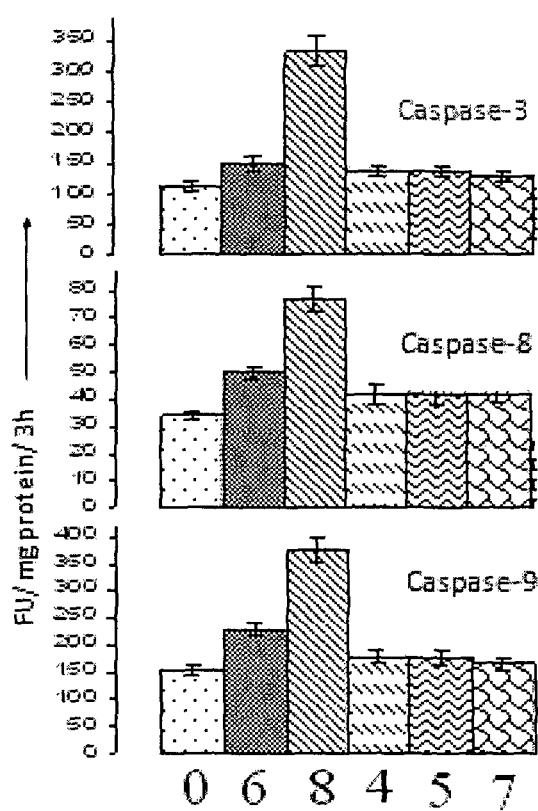
FIG. 3 shows Different caspases estimation in HL-60 cells.

All the compounds have exhibited apoptosis induction in the AnnexinV flow cytometric assay. To investigate the mechanism of these compounds were also evaluated for their ability to induce caspase-3, caspase-8, caspase-9 activity in HL-60 Cells (FIG. 4) compound 8 used at 1 µM concentrations in HL-60 cells activated caspases-3,-8,-9 activities by 2-3 folds (FIG. 3); whereas other tested compounds which showed little apoptosis induction in the AnnexinV assay was similarly ineffective or very limited activation of caspases. So activation of caspases by compound 8 indicate that it induce apoptosis through both the intrinsic as well as extrinsic apoptotic pathway in HL-60 cells.

5. DNA Fragmentation

Figure 4:
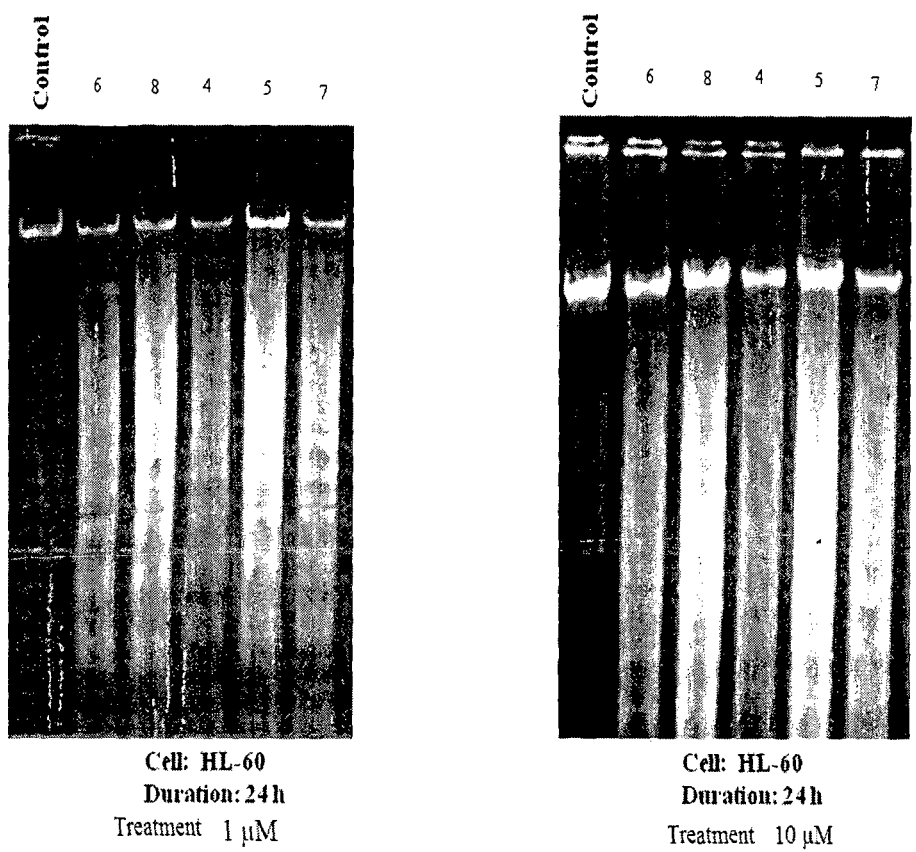
FIG. 4 shows DNA fragmentation in HL-60 cells at two concentrations namely 1 µM and 10 µM for 24 h.
Figure 5:
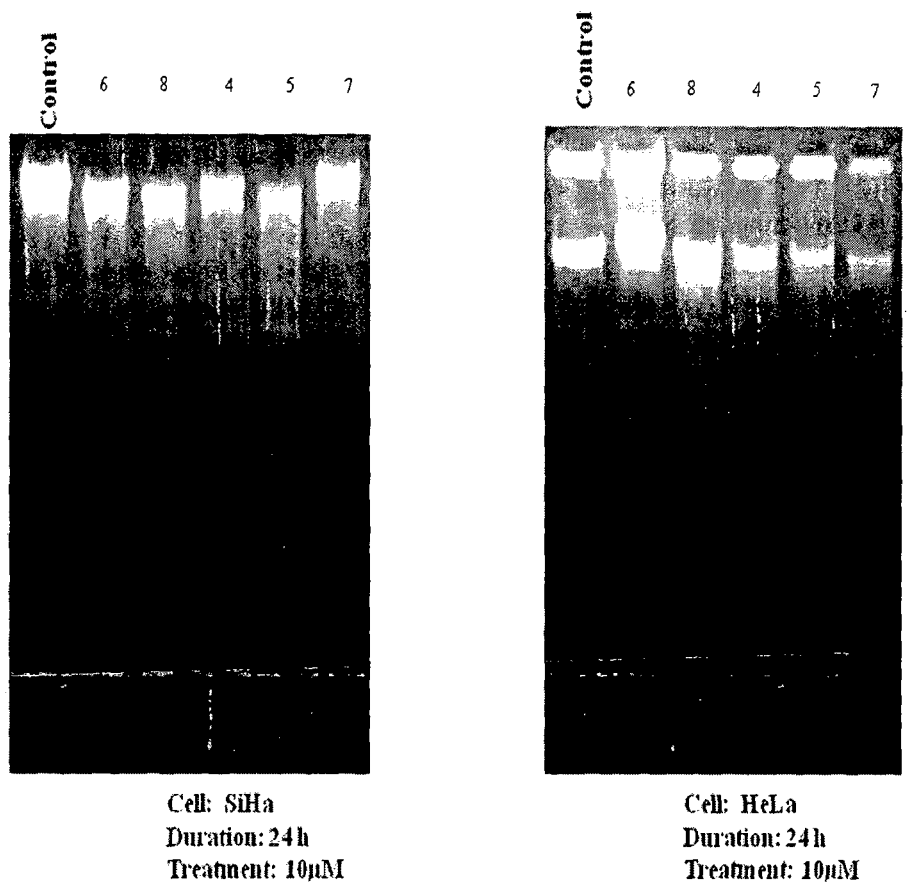
FIG. 5 shows DNA fragmentation in cervical cancer SiHa and HeLa cells.

All the tested compounds induce DNA fragmentation (i.e. characteristic ladder pattern) in HL-60 Cells at 1 µM and 10 µM. While no laddering was observed in cervical cancer SiHa and HeLa cell expose at higher concentrations (10 µM) indicates these compounds specifically target the leukemia HL-60 cells (FIG. 4, 5).

6. Cell Cycle Analysis (FACS) Measured by Flow Cytometry

Figure 6:
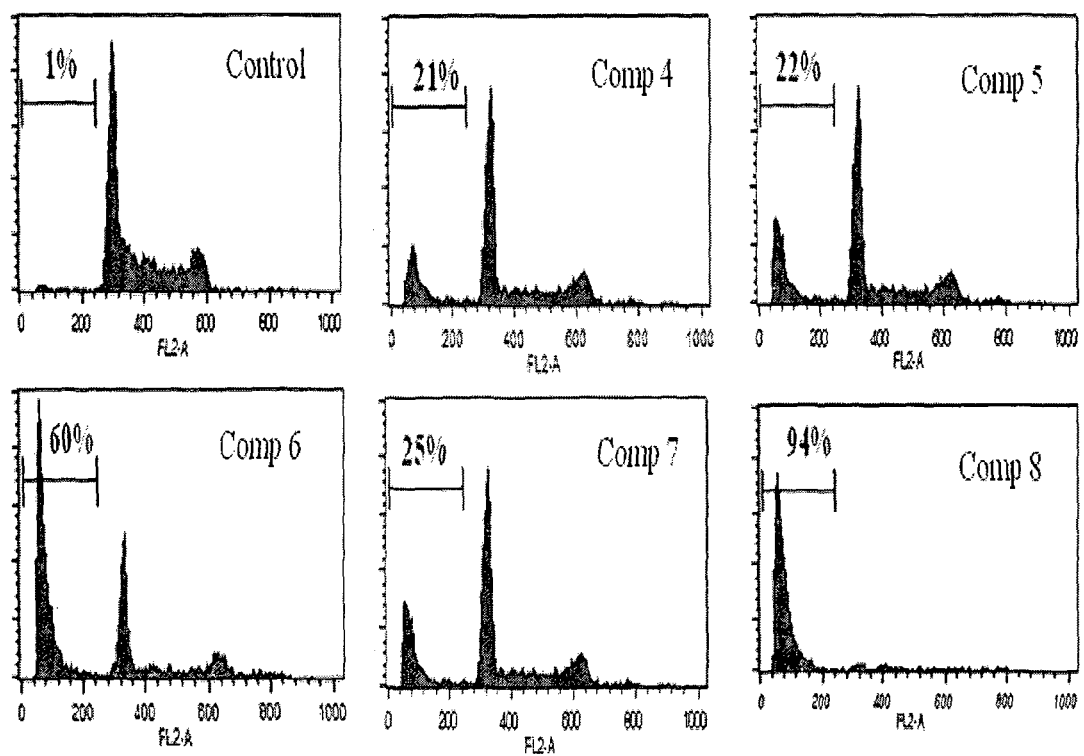
FIG. 6 shows Cell cycle analysis in HL-60 cells.

HL-60 cells exposed to 1 µM concentration of these compounds for up to 24 h exhibited continuous increase in sub-G0 fraction which may comprise both apoptotic and debris fraction implying together the extent of cell death (FIG. 6). The damage was more apparent with compound 8 and 6 (90% and 60% DNA damaged, respectively). These compounds did not produce mitotic block or delay in cell cycle and there was a significant fall in relative PI fluorescence of cell fractions in all the three phases G1, S and G2/M, which indicated that decrease in DNA fluorescence is not cell cycle selective.

7. Flow Cytometric Analysis of Reactive Oxygen Species (ROS)

Figure 7:
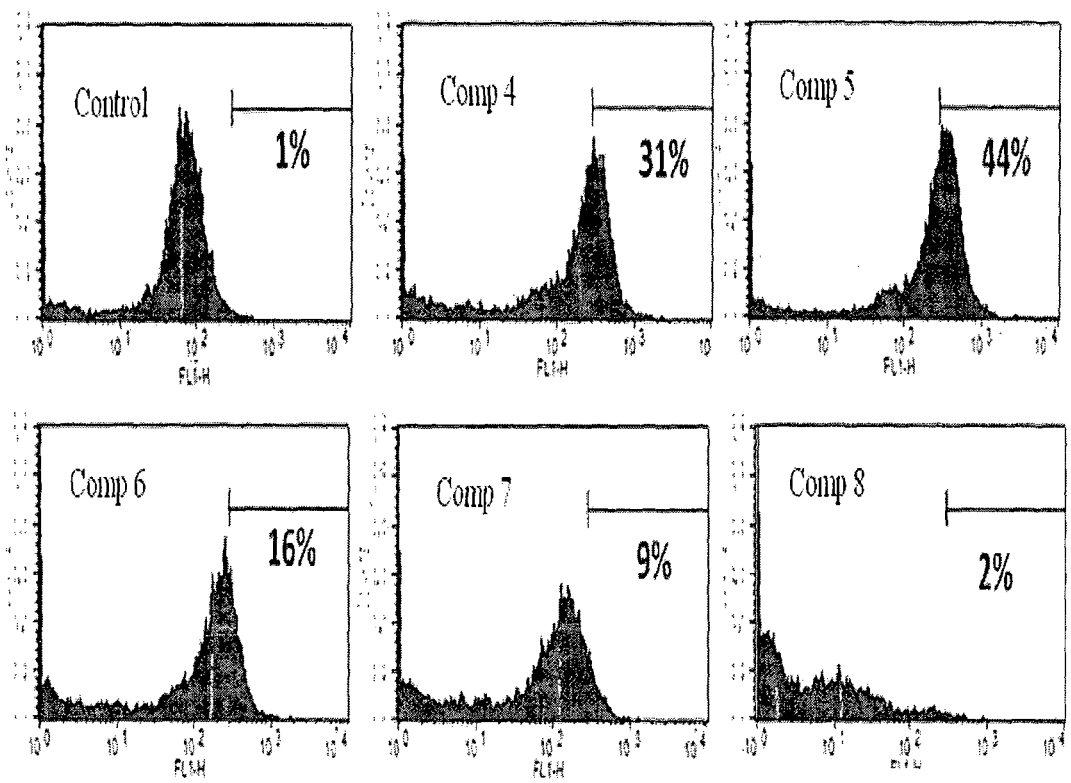
FIG. 7 shows ROS analysis in HL-60 cells.

It was clear that these compounds were cytotoxic and induce apoptosis in HL-60 cells, now we have to found out the early events which were responsible for the induction of apoptosis like reactive oxygen species (ROS) or nitric oxide (NO) generation. Intracellular peroxide (ROS) in the cells was measured by DCFH-DA by using flow cytometry. Cells were incubated with tested compounds at 1 µM for 24 h in HL-60 cells and analyzed by flow cytometry after double staining with DCFH-DA (FIG. 7). Cells were analyzed for fluorescence intensity in FL1 vs. cell count. There was hardly any DCF fluorescence (ROS positive cells) in the untreated HL-60 cells, and this status remained unchanged when cells were incubated for 24 hr with compounds 7 and 8. There was a significant increase of ~44% in DCF positive cell population with compound 5 as compare to control. Compounds 4 and 6 also induce the generation of peroxide in HL-60 cells (31 and 16% increase, respectively).

8. Endogenous Nitric Oxide Generation in Leukemia Cells

Figure 8:
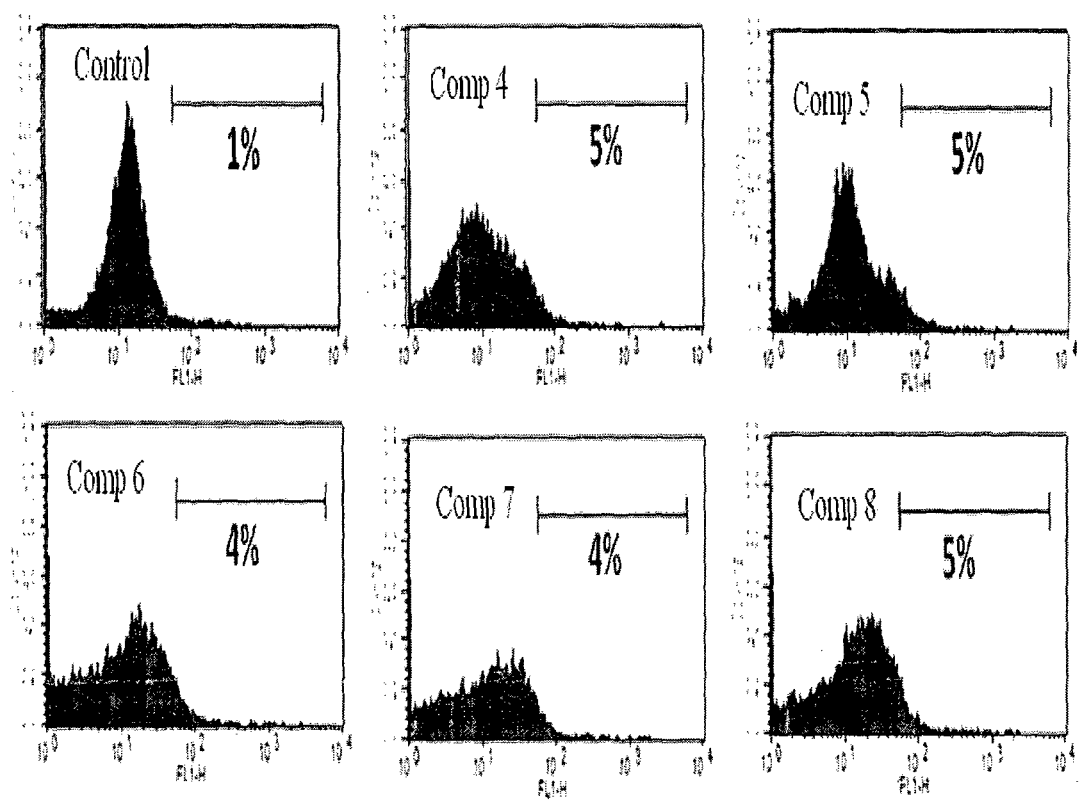
FIG. 8 shows Nitric oxide analysis in HL-60 cells.

To analyze death pathways induced by these tested compounds in HL-60 cells, we found out the level of nitric oxide induction by employing nitric oxide binding dye DAF-2DA. Cells were exposed to tested compounds for 24 h at 1 µM and NO level was analyzed by bivariate plots of NO vs. counts. No tested compounds induce the level of nitric oxide in HL-60 cells, so there was possibility of other events in induction of apoptosis (FIG. 8).

9. Loss of Mitochondrial Membrane Potential

Figure 9:
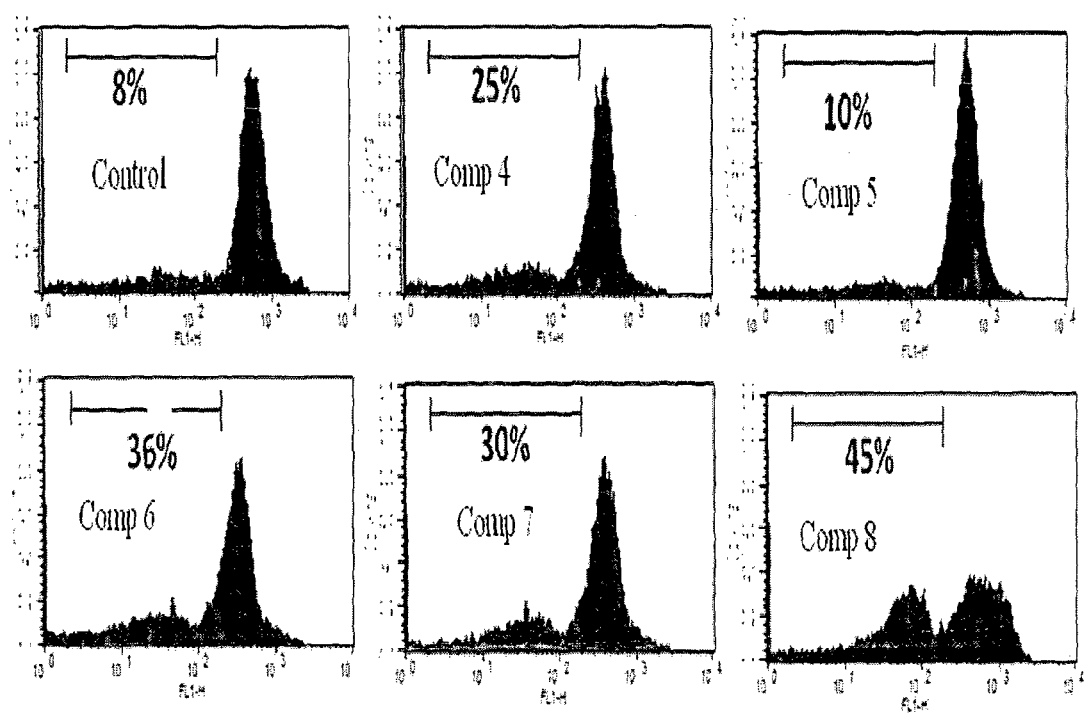
FIG. 9 shows Loss of mitochondrial membrane potential in HL-60 cells.

Rhodamine-123 uptake into mitochondria is driven by mitochondrial Transmembrane potential ($\Psi_{mt}$) that allows the determination of cell population with active integrated mitochondrial functions. Loss of $\Psi_{mt}$ leads to depolarization of mitochondrial membranes leading to collapse of mitochondrial functions ensuing cell death. The loss of $\Psi_{mt}$ indicated the loss of mitochondrial integrity to couple electrons to energy production. HL-60 cells exposed to tested compounds for 48 h at 1 µM were analyzed for Rh-123 uptake by flow cytometry. The percentage of cells with low Rh-123 quantum fluorescence indicative of loss of $\Psi_{mt}$ was calculated among the total acquired cell events (10,000). In the untreated control cells, more than 90% cells were functionally active with high Rh-123 signals (FIG. 9). Compound 4, 6-8 induce loss of mitochondria membrane potential in HL-60 cells in which compound 8 have highest potential (45% loss).

10. Immunoblot Analysis of Various Cell Death Targets

Figure 10:
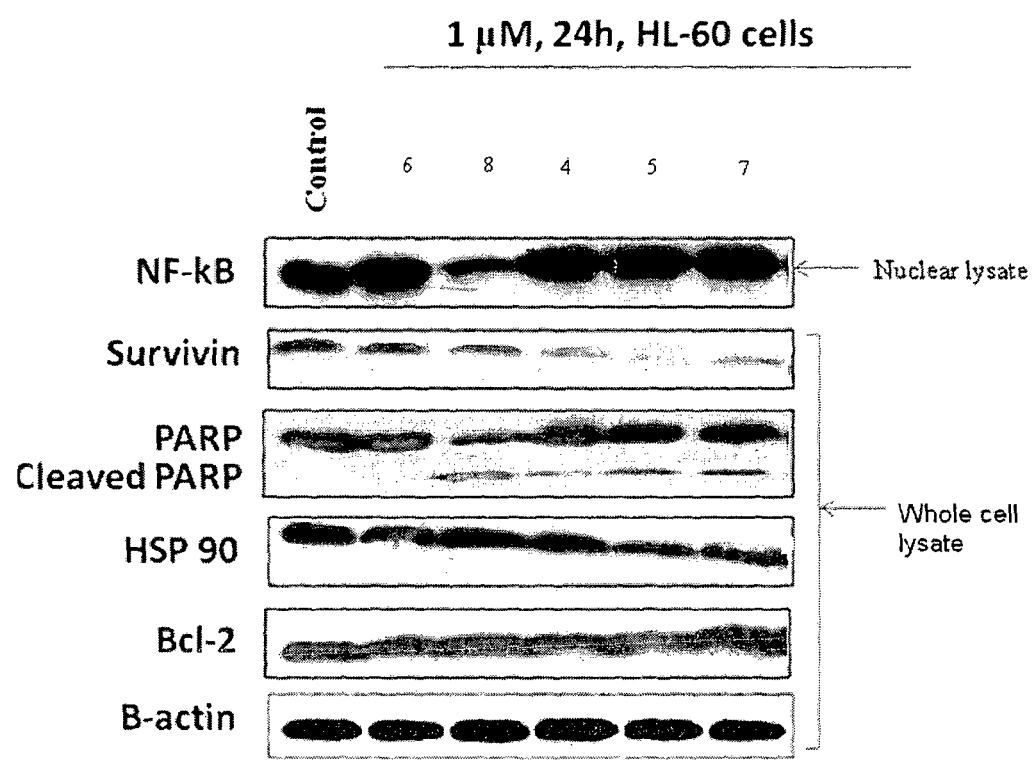
FIG. 10 shows Different caspases estimation in HL-60 cells.

Apoptosis was further characterized by the western blot analysis. Cells were treated with tested compounds at 1 µM for 24 h and expression of key apoptotic proteins like NF-kB, survivin; PARP, Bcl-2 and HSP-90 were analyzed through western blot. Both NF-kB and survivin are highly expressed in HL-60 cells. NF-kB is a transcriptional factor regulating the expression of several genes in the cells whereas survivin is a cell cycle regulated inhibitor of apoptosis protein (IAP), mostly over expressed in most of the tumors. Compound 8 significantly inhibit the expression of NF-kB in HL-60 cells whereas rests of the compounds have no effect on NF-kB level (FIG. 10). Almost all the tested compounds inhibit the survivin level but compound 6 have highest inhibition potential among them.

During apoptotic stimuli activated caspase-3 appears to cause DNA fragmentation through activation of caspase activated DNAse (CAD) in the nucleus of the cells. Activated caspase-3 also used poly ADP ribose polymerase (PARP) as a substrate and consequently induced its cleavage, from 116 kDa to 89 kDa. All the tested compounds induce the PARP cleavage but compound 8 has the highest potential among them in HL-60 cells. Inspite of NF-kB, survivin, PARP some of the compounds (4-6) significantly inhibit the expression of heat shock protein like HSP-90 in HL-60. Cancer cells have very high level of heat shock proteins. These are molecular chaperones expressed constitutively under normal conditions to maintain protein homeostasis and are induced upon environmental stress.

Interestingly, all the tested compounds did not inhibit the Bcl-2 level in HL-60 cells (FIG. 10), as evident by the loss of mitochondrial membrane potential by some of the compounds. So there was possibility that other Bcl-2 family proteins will be involve in the induction of apoptosis by these compounds in HL-60 cells.

11. DNA Topoisomerase-II Inhibition Assay

Figure 11:
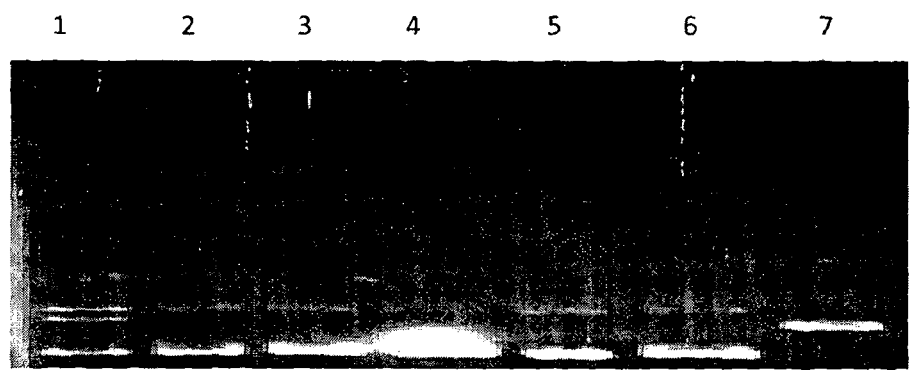
FIG. 11 shows Topoisomerase-II Inhbition assay. Lane 1 treatment of DNA with Etoposide (100 µM) and Lanes 2, 3, 4, 5, 6: DNA treatments with compounds 6, 8, 4, 5 and 7 respectively (1 µM each). Lane 7: Linear DNA only.

DNA topoisomerases are nuclear enzymes capable of resolving the topology of DNA to allow its replication. So, proper relaxing is very important for successful replication cycle and thus for the cell survival. However, topoisomerases also serve as targets in the anticancer chemotherapy in which cell death serves an important purpose. Moreover, the topoisomerase targeting drugs can either be classified either topo posions, which act by stabilizing enzyme DNA cleavable complexes leading to DNA break or topo catalytic inhibitors, which act by stabilizing enzyme where both DNA strands remain intact and no DNA breaks occur. Importantly, all the topoisomerase inhibitors finally induce apoptosis. In the present study, all the five compounds 4-8 were first subjected to topoisomerase II inhibition assay. As depicted by FIG. 11 the data revealed that all the different compounds resulted in topoisomerase-II inhibition to significant extent; however, 8, 4, 5, 7 showed more potent effect relative to etoposide on DNA relaxation induced by topoisomerase in presence of these compounds at 1 µM concentration.

12. Scanning Electron Microscopic (SEM) Analysis of Cell Death Induced by Compd. 8

The HL-60 cells were seeded in 6-well tissue culture plates at the density of $2 \times 10^5$ cells per ml in complete medium supplemented with 10% FCS in the presence and absence (as controls) of compd. 8 at 0.5 and 1 µM for 24-48 h. After 24 h, culture was incubated with the compound for 6, 12, 24 and 48 h. The stock solution was prepared in DMSO and added to the medium to achieve the desired final concentration. Control samples were treated with DMSO vehicle alone. To assess the mechanism of cell death, after incubation for specified time at 37° C., the cells were processed for SEM studies.

For SEM, HL-60 cells, were sedimented at 1800 rpm for 10 min. Cell pellets were fixed immediately with 2.5% glutaraldehyde in 0.1M phosphate buffer (pH 7.2) at 4° C. for 1 h, post-fixed with 1% $OsO_4$ for 1 h in the same buffer, dehydrated with graded ethanol solutions and dried in a critical point drier using $CO_2$ (Blazer's Union) and coated with gold using a Sputter coater (Polaron). The specimens were examined with a JEOL-100CXII electron microscope with ASID at 40 KV.

Figure 12:
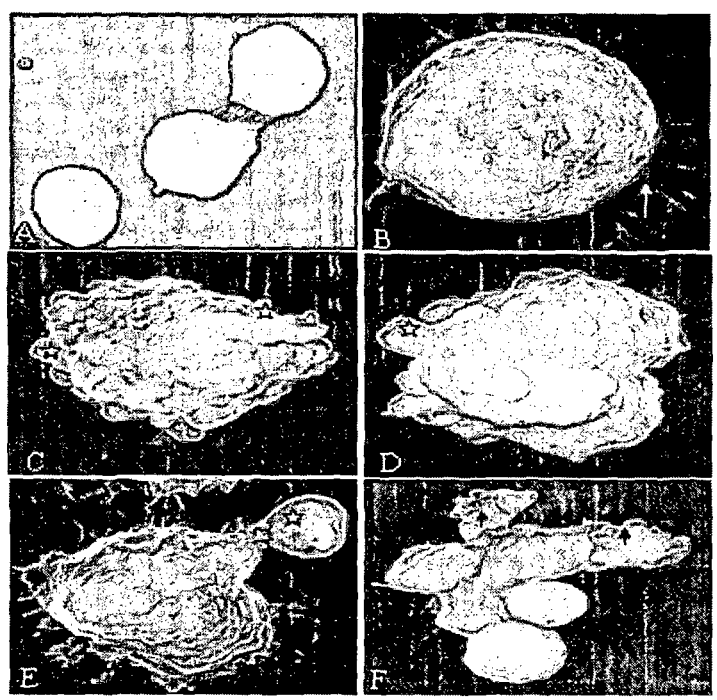
FIG. 12 shows A-F. SEM of control (A, B) and compound 8 treated (C—F) HL-60 cells showing surface ultra structure. The control cells show microvilli on cell surface (B, arrow), The treatment (1 µM) after 12 h causes smoothening of cell surface, condensation in size and blebbing of plasma membrane (C-D, asterisk) and after 24 h apoptotic bodies were seen budding from the cell (E, asterisk) and some of the cells were completely transformed into apoptotic bodies (F, arrowhead). (Magnification A, F, 4000×, B-E, 8000×).

SEM examination revealed that HL-60 cells were spherical in shape having microvilli on entire surface and with a few surface projections (FIG. 12, B, arrow). The compound 8 incubation of the cells at 1 µM after 12 h caused, decrease in size, smoothening of surface and blebbing of plasma membrane in majority of cells (FIG. 12, C-D, asterisk). After 24 h incubation, the apoptotic bodies were seen budding from the cell surface (FIG. 12E, asterisk) and some of the cells were completely transformed into apoptotic bodies (FIG. 12, F, arrowhead). At 0.5 µM, apoptosis was seen only in few cells after 48 h of treatment.

13. Fluorescent Microscopic Analysis of Cell Death Induced by Compound 9

The mechanism of cell death was also studied in HL-60 and PC-3 cells by fluorescent microscopic studies. The PC-3 cells were treated with compd. 8 as in case of HL-60 cells. For fluorescent DAPI staining, air dried smears of cells on glass slides were fixed in absolute methanol at −20° C. for 20 min and stained with DAPI (Sigma) at 1 µg/ml at room temperature for 20 min in the dark and mounted with 90% glycerol in PBS and observed under fluorescent microscope (Olympus).

Figure 13:
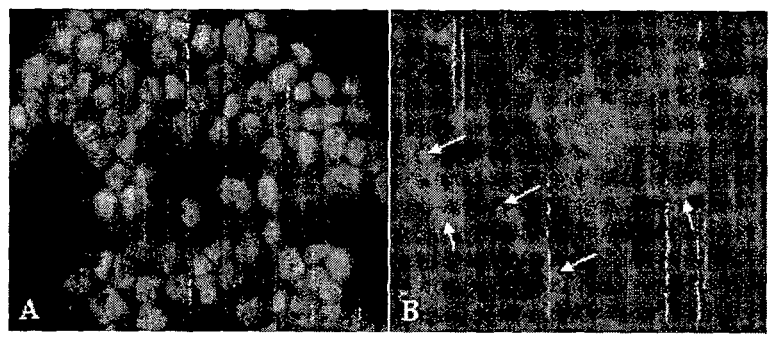
FIG. 13 shows Morphological changes in PC-3 cells treated with 1 µM, compound. 8 for 24 h: The cells were stained with DAPI and observed under fluorescent microscope. (A) Untreated control cells showing large sized nuclei. (B) The cells treated for 24 h indicate condensation and fragmentation of nuclei (arrow) due to apoptosis (Magnification: A-B, 400×).

Morphological changes of HL-60 and PC-3 cells in response to this compound 8 were observed. The untreated cells were having large sized nuclei. The incubation for 24 at 1 µM of the compound 8 revealed fragmentatation of nuclei due to apoptosis both in HL-60 (data not shown) and PC-3 cells (FIG. 13, B).

2. Biological Activity of 2-anilino nicotinyl Linked 2-amino benzothiazole Conjugates In vivo Cytotoxicity
Model: Ehrlich Ascites Carcinoma (EAC)
Animals: Swiss
Sex: Female
Weight: 18-23 g Ehrlich ascites carcinoma (EAC) cells were collected from the peritoneal cavity of the swiss mice harbouring 8-10 days old ascitic tumor. $1 \times 10^7$ EAC cells were injected intraperitoneally in Swiss mice selected for the experiment on day 0. The next day, animals were randomized and divided into different groups. The treatment groups contained 7 animals each and control group contained 10 animals. Treatment groups were treated with different doses of test substances intraperitoneally from day 1-9. One of the treatment group received 5-fluorouracil (20 mg/kg, i.p) and it served as positive control. The tumor bearing control group was similarly administered normal saline (0.2 ml, i.p.). On day 12, animals were sacrificed and ascitic fluid was collected from peritoneal cavity of each mouse for the evaluation of tumor growth. Percent tumor growth inhibition was calculated based on the total number of tumor cells present in the peritoneal cavity as on day 12 of the experiment using the following formula.

$$\text{Percent tumor growth inhibition} = \frac{\text{Av. no. of cells in control group} - \text{Av. no. of cells in treated group}}{\text{Av. no. of cells in control group}} \times 100$$

TABLE 6

In vivo anticancer activity of against ehrlich ascites carcinoma (EAC)

| Sample No. | Model | Dose | Growth Inhibition (%) | No. of deaths |
|---|---|---|---|---|
| Comp 4 | Ehrlich Ascites Carcinoma (EAC) | 50 mg/Kg | Intolerable | 7/7 |
|  |  | 10 mg/Kg | 42.21 | 2/7 |
| Comp 5 | Ehrlich Ascites Carcinoma (EAC) | 30 mg/Kg | Intolerable | 7/7 |
|  |  | 5 mg/Kg | 20.90 | 0/7 |

TABLE 6-continued

In vivo anticancer activity of against ehrlich ascites carcinoma (EAC)

| Sample No. | Model | Dose | Growth Inhibition (%) | No. of deaths |
|---|---|---|---|---|
| Comp 6 | Ehrlich Ascites Carcinoma (EAC) | 20 mg/Kg | 22.18 | 0/7 |
|  |  | 40 mg/Kg | 68.11 | 4/7 |
|  |  | 30 mg/Kg | 43.11 | 0/7 |
| Comp 7 | Ehrlich Ascites Carcinoma (EAC) | 20 mg/Kg | 63.89 | 0/7 |
|  |  | 40 mg/Kg | Intolerable | 7/7 |
| Comp 8 | Ehrlich Ascites Carcinoma (EAC) | 20 mg/Kg | Intolerable | 7/7 |
|  |  | 5 mg/Kg | Intolerable | 7/7 |
|  |  | 2 mg/Kg | Intolerable | 7/7 |
|  |  | 0.5 mg/kg | Intolerable | 7/7 |
|  |  | 0.1 mg/kg | 10.98 | 0/7 |
|  |  | 0.3 mg/kg | 53.15 | 0/7 |
|  |  | 0.4 mg/kg | Intolerable | 7/7 |

Compound 4 was, found to be toxic at 0.50 mg/Kg dose. It however exhibited 42.21% anticancer activity against EAC at 10 mg/Kg. It seems to be the maximum anticancer potential of this compound as deaths of 2 animals were recorded out of 7 animals in the group and further increase in dose would have resulted in toxicity to more number of animals.

Compound 5 was toxic to animals at a dose of 30 mg/kg as all the seven animals in the group died during the course of 9 days treatment. This compound showed 20.90 percent tumor growth inhibition at 5 mg/kg dose level. This compound may yield higher level of anticancer activity at 10 or 15 mg/kg doses.

Compound 6 exhibited 22.18, 43.11 and 68.11 percent inhibition in the growth of EAC at 20, 30 and 40 mg/kg i/p. This compound showed maximum activity of 68.11 percent accompanied by considerable toxicity to animals (deaths 4/7).

Compound 7 exhibited considerably good anticancer activity of 63.89 percent at 20 mg/kg i/p dose without any deaths. Thus, this compound qualifies for further studies.

Compound 8 has good anticancer activity and is highly toxic also. As can be seen from the table, the compound exhibited good anticancer activity of 53.15 percent at 0.3 mg/kg i/p dose level. ° However, little increase in dose to 0.4 mg/kg resulted in deaths of all the seven animals in the group. All other doses higher than 0.4 mg/kg have been highly toxic to animals.

Compound 7 seems to be the best as it has very good anticancer activity without adversely affecting experimental animals at a dose of 20 mg/Kg i/p.

The 2-anilino nicotinyl 2-amino benzothiazole conjugates exhibited significant cytotoxic activity against the tested human cancer cell lines. Some of these conjugates exhibiting as apoptosis inducers. Among these the compound 8 significantly useful as anticancer agent and apoptosis inducer

ADVANTAGES OF THE INVENTION

1. The present invention provides 2-anilino nicotinyl 2-amino benzothiazole conjugates of general formula A.
2. It also provides a process for the preparation of 2-anilino nicotinyl linked 2-amino benzothiazole conjugates of general formula A.

We claim:
1. A 2-anilino nicotinyl linked 2-amino benzothiazole conjugate of general formula A

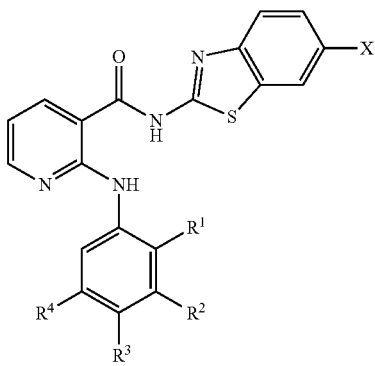

General formula A wherein (1) $R^1$=H or Cl; $R^2$=H, $OCH_3$ or F; $R^3$=H, $OCH_3$, F or Cl; $R^4$=H, $OCH_3$ or F, and X=F;
(2) $R^1$=H or Cl; $R^2$=$OCH_3$, $R^3$=H, $OCH_3$, F or Cl; $R^4$=H or $OCH_3$ and X=$OCH_3$, F or $NO_2$, or
(3) $R^1$=H or Cl; $R^2$=H or $OCH_3$, $R^3$=H, $OCH_3$, F or Cl; $R^4$=$OCH_3$ and X=$OCH_3$, F or $NO_2$.

2. The 2-anilino nicotinyl linked 2-amino benzothiazole conjugate of claim 1, wherein the conjugate has a structural formula selected from a group consisting of:

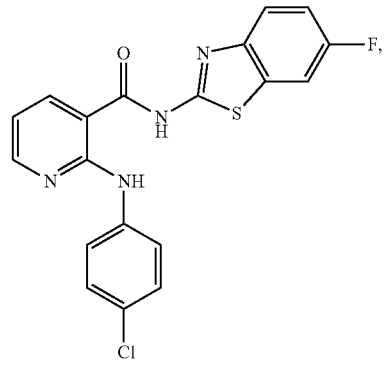

9

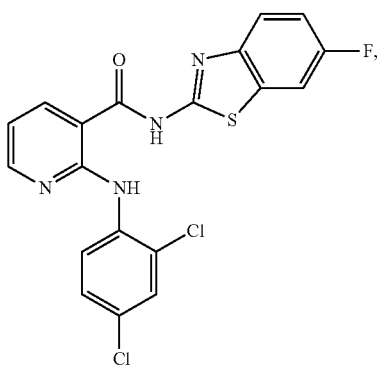

10

-continued

11

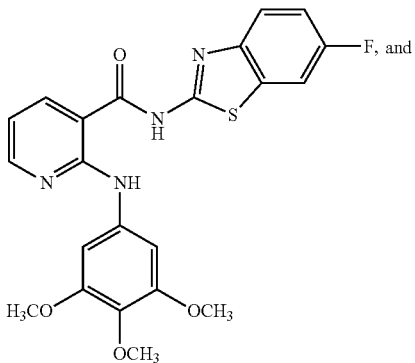

12

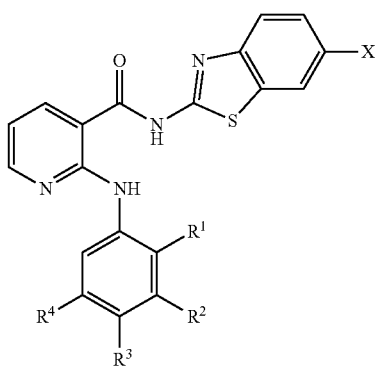

3. A process for the preparation of 2-anilino nicotinyl linked-amino benzothiazole conjugates of general formula A General formula A

[Structure of General formula A]

wherein $R^1$=H or Cl; $R^2$=OCH$_3$; $R^3$=H, OCH$_3$, F or Cl; $R^4$=H, OCH$_3$ and X=F, said process comprising the steps of:
i. refluxing 2-chloro nicotinic acid ethyl ester with substituted anilines at a temperature in the range of 150° to 160° for a time period in the range of 5 to 6 hours, wherein $R^1$ represents hydrogen, chloro $R^2$ represents methoxy, $R^3$ represents hydrogen, fluoro, chloro, methoxy and $R^4$-represents hydrogen, or methoxy

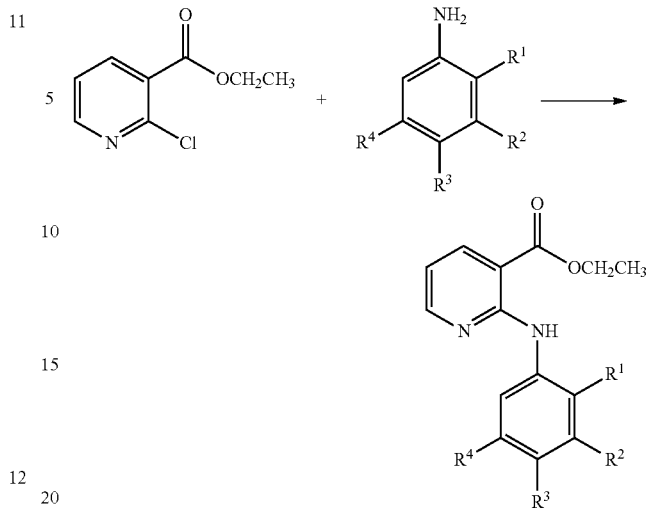

in ethylene glycol to give the coupled 2-anilino nicotinic acid esters;

ii. treating 2-anilino nicotinic acid esters as obtained in step (i) with NaOH solution in organic solvent to obtain sodium salt of 2-anilino nicotinic acid which on treatment with HCl form 2-anilino nicotinic acids wherein $R^1$ represents hydrogen, chloro, $R^2$ represents methoxy, $R^3$ represents hydrogen, fluoro, chloro, methoxy and $R^4$ represents hydrogen, methoxy;

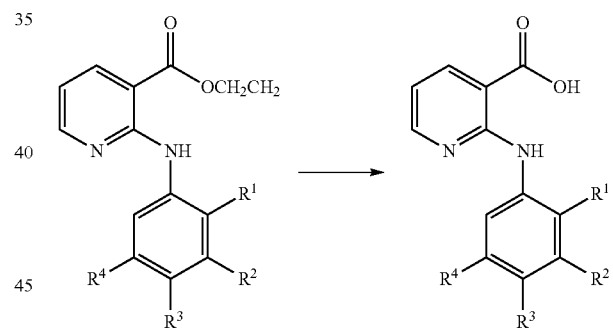

iii. treating 2-anilino nicotinic acids obtained in step (ii) and 6-substituted 2-amino benzothiazoles with EDCl/HOBt in dry DMF to obtain compounds of general formula A.

-continued

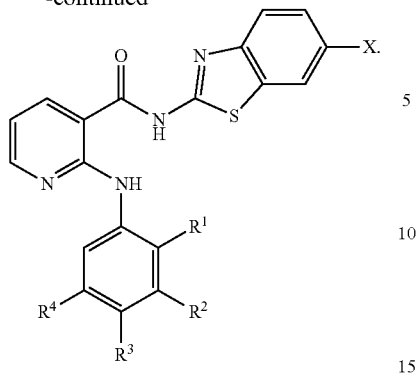

4. The process as claimed in claim 3, wherein the organic solvent used in step (ii) is selected from a group consisting of methanol and ethanol.

5. The 2-anilino nicotinyl linked 2-amino benzothiazole conjugate of claim 1, wherein $R^2$=OCH$_3$ and $R^4$=H or OCH$_3$, or $R^2$=H or OCH$_3$ and $R^4$=OCH$_3$.

6. The 2-anilino nicotinyl linked 2-amino benzothiazole conjugate of claim 1, wherein X=F.

* * * * *